(12) United States Patent
Kim

(10) Patent No.: US 12,708,315 B2
(45) Date of Patent: Aug. 18, 2026

(54) ARRHYTHMIA DETECTION IN A WEARABLE MEDICAL SYSTEM

(71) Applicant: West Affum Holdings DAC, Dublin (IE)

(72) Inventor: Jaeho Kim, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 518 days.

(21) Appl. No.: 18/313,218

(22) Filed: May 5, 2023

(65) Prior Publication Data

US 2024/0041381 A1 Feb. 8, 2024

Related U.S. Application Data

(60) Provisional application No. 63/395,282, filed on Aug. 4, 2022.

(51) Int. Cl.
*A61B 5/363* (2021.01)
*A61B 5/308* (2021.01)
(Continued)

(52) U.S. Cl.
CPC .............. *A61B 5/363* (2021.01); *A61B 5/308* (2021.01); *A61B 5/352* (2021.01); *A61B 5/366* (2021.01); *A61N 1/365* (2013.01); *A61N 1/3904* (2017.08)

(58) Field of Classification Search
CPC ......... A61B 5/363; A61B 5/308; A61B 5/366; A61B 5/4836; A61N 1/3904; A61N 1/046; A61N 1/0484; A61N 1/3993
See application file for complete search history.

(56) References Cited

U.S. PATENT DOCUMENTS 3,724,355 A 4/1973 Busch et al.
3,724,455 A 4/1973 Unger
(Continued)

FOREIGN PATENT DOCUMENTS

DE 102005060985 A2 6/2007
EP 2305110 A1 4/2011
(Continued)

OTHER PUBLICATIONS

Heartstart MRx and XL AED Algorithm—Application Note, Jul. 2001, Edition 2 Philips Healthcare, USA.
(Continued)

*Primary Examiner* — Catherine M Voorhees
(74) *Attorney, Agent, or Firm* — Seed Intellectual Property Law Group LLP

(57) ABSTRACT

A wearable medical system detects cardiac arrythmia condition of a patient. The wearable medical system comprises a support structure, a plurality of ECG electrodes to sense an ECG signal, and an energy output device to store an electrical charge. The wearable medical system further comprises an output circuit coupled to the energy output device, a plurality of therapy electrodes, and a processor. The plurality of therapy electrodes is coupled to the support structure and the output circuit and delivers therapy to the patient. The processor is coupled to the plurality of ECG electrodes and the output circuit. The processor comprises a QRS detector module that has a first threshold and a second threshold. The QRS detector module comprises first and second QRS detectors that analyze the ECG signals for the first and second thresholds, respectively. The first and second thresholds are configured to detect tachyarrhythmia and bradyarrhythmia, respectively.

18 Claims, 6 Drawing Sheets

(51) Int. Cl.

| | |
|---|---|
| *A61B 5/352* | (2021.01) |
| *A61B 5/366* | (2021.01) |
| *A61N 1/365* | (2006.01) |
| *A61N 1/39* | (2006.01) |

(56) References Cited

U.S. PATENT DOCUMENTS 4,583,524 A 4/1986 Hutchins
4,619,265 A 10/1986 Morgan et al.
4,666,432 A 5/1987 McNeish et al.
4,698,848 A 10/1987 Buckley
4,928,690 A 5/1990 Heilman et al.
4,955,381 A 9/1990 Way et al.
5,078,134 A 1/1992 Heilman et al.
5,228,449 A 7/1993 Christ et al.
5,348,008 A 9/1994 Bomnn et al.
5,353,793 A 10/1994 Bomn
RE34,800 E 11/1994 Hutchins
5,394,892 A 3/1995 Kenny et al.
5,405,362 A 4/1995 Kramer et al.
5,429,593 A 7/1995 Matory
5,474,574 A 12/1995 Payne et al.
5,618,208 A 4/1997 Crouse et al.
5,662,690 A 9/1997 Cole et al.
5,708,978 A 1/1998 Johnsrud
5,741,306 A 4/1998 Glegyak et al.
5,782,878 A 7/1998 Morgan et al.
5,792,204 A 8/1998 Snell
5,902,249 A 5/1999 Lyster
5,913,685 A 6/1999 Hutchins
5,944,669 A 8/1999 Kaib
6,047,203 A 4/2000 Sackner et al.
6,065,154 A 5/2000 Hulings et al.
6,108,197 A 8/2000 Janik
6,148,233 A 11/2000 Owen et al.
6,201,992 B1 3/2001 Freeman
6,263,238 B1 7/2001 Brewer et al.
6,280,461 B1 8/2001 Glegyak et al.
6,287,328 B1 9/2001 Snyder et al.
6,304,780 B1 10/2001 Owen et al.
6,319,011 B1 11/2001 Motti et al.
6,334,070 B1 12/2001 Nova et al.
6,356,785 B1 3/2002 Snyder et al.
6,427,083 B1 7/2002 Owen et al.
6,437,083 B1 8/2002 Brack et al.
6,450,942 B1 9/2002 Apanashvili et al.
6,529,875 B1 3/2003 Nakajima et al.
6,546,285 B1 4/2003 Owen et al.
6,671,545 B2 12/2003 Fincke
6,681,003 B2 1/2004 Linder et al.
6,762,917 B1 7/2004 Verbiest et al.
7,065,401 B2 6/2006 Worden
7,099,715 B2 8/2006 Korzinov
7,212,850 B2 5/2007 Prystowsky
7,559,902 B2 7/2009 Ting et al.
7,587,237 B2 9/2009 Korzinov
7,753,759 B2 7/2010 Pintor et al.
7,865,238 B2 1/2011 Brink
7,870,761 B2 1/2011 Valentine et al.
7,907,996 B2 3/2011 Prystowsky
7,941,207 B2 5/2011 Korzinov
7,974,689 B2 7/2011 Volpe et al.
8,135,462 B2 3/2012 Owen et al.
8,140,154 B2 3/2012 Donnelly et al.
8,369,944 B2 2/2013 Macho et al.
8,527,028 B2 9/2013 Kurzweil et al.
8,548,557 B2 10/2013 Garstka et al.
8,560,044 B2 10/2013 Kurzweil et al.
8,615,295 B2 12/2013 Savage et al.
8,644,925 B2 2/2014 Volpe et al.
8,676,313 B2 3/2014 Volpe et al.
8,706,255 B2 4/2014 Phillips et al.
8,742,349 B2 6/2014 Urbon et al.
8,897,860 B2 11/2014 Volpe et al.
8,904,214 B2 12/2014 Volpe et al.
8,965,500 B2 2/2015 Macho et al.
9,008,801 B2 4/2015 Kaib et al.
9,084,583 B2 7/2015 Mazar et al.
9,089,685 B2 7/2015 Sullivan et al.
9,119,547 B2 9/2015 Cazares et al.
9,131,901 B2 9/2015 Volpe et al.
9,132,267 B2 9/2015 Kaib
9,265,432 B2 2/2016 Warren et al.
9,345,898 B2 5/2016 Piha et al.
9,408,548 B2 8/2016 Volpe et al.
9,445,719 B2 9/2016 Libbus et al.
9,454,219 B2 9/2016 Volpe et al.
9,579,020 B2 2/2017 Libbus et al.
9,592,403 B2 3/2017 Sullivan
9,598,799 B2 3/2017 Shoshani et al.
9,675,804 B2 6/2017 Whiting et al.
9,878,171 B2 1/2018 Kaib
9,895,105 B2 2/2018 Romem
9,901,741 B2 2/2018 Chapman et al.
RE46,926 E 7/2018 Bly et al.
10,016,613 B2 7/2018 Kavounas
10,076,656 B2 9/2018 Dar et al.
10,192,387 B2 1/2019 Brinig et al.
10,307,133 B2 6/2019 Kaib
10,463,867 B2 11/2019 Kaib et al.
10,589,110 B2 3/2020 Oskin et al.
10,599,814 B2 3/2020 Landrum et al.
2002/0181680 A1 12/2002 Linder et al.
2003/0158593 A1 8/2003 Heilman et al.
2005/0107833 A1 5/2005 Freeman et al.
2005/0107834 A1 5/2005 Freeman et al.
2006/0173499 A1 8/2006 Hampton et al.
2008/0140159 A1* 6/2008 Bornhoft .............. A61B 5/0006 607/60
2008/0312709 A1 12/2008 Vollpe et al.
2009/0005827 A1 1/2009 Weintraub et al.
2010/0007413 A1 1/2010 Herleikson et al.
2010/0114213 A1* 5/2010 Doerr .................. A61B 5/7264 607/5
2010/0298899 A1 11/2010 Donnelly et al.
2011/0022105 A9 1/2011 Owen et al.
2011/0288604 A1 11/2011 Kaib et al.
2011/0288605 A1 11/2011 Kaib et al.
2012/0112903 A1 5/2012 Kaib et al.
2012/0144551 A1 6/2012 Guldalian
2012/0150008 A1 6/2012 Kaib et al.
2012/0158075 A1 6/2012 Kaib et al.
2012/0191476 A1 7/2012 Reid et al.
2012/0265265 A1 10/2012 Razavi et al.
2012/0283794 A1 11/2012 Kaib et al.
2012/0293323 A1 11/2012 Kaib et al.
2012/0302860 A1 11/2012 Volpe et al.
2012/0310315 A1 12/2012 Savage et al.
2013/0085538 A1 4/2013 Volpe et al.
2013/0144355 A1 6/2013 Macho et al.
2013/0231711 A1 9/2013 Kaib
2013/0245388 A1 9/2013 Rafferty et al.
2013/0274565 A1 10/2013 Langer et al.
2013/0317852 A1 11/2013 Worrell et al.
2013/0325078 A1 12/2013 Whiting et al.
2014/0012144 A1 1/2014 Crone
2014/0025131 A1 1/2014 Sullivan et al.
2014/0046391 A1 2/2014 Cowan et al.
2014/0070957 A1 3/2014 Longinotti-Buitoni et al.
2014/0163663 A1 6/2014 Poddar et al.
2014/0324112 A1 10/2014 Macho et al.
2014/0378812 A1 12/2014 Saroka et al.
2015/0039053 A1 2/2015 Kaib et al.
2015/0161554 A1 6/2015 Sweeney et al.
2015/0297135 A1 10/2015 Shoshani et al.
2015/0328472 A1 11/2015 Sullivan et al.
2016/0004831 A1 1/2016 Carlson et al.
2016/0076175 A1 3/2016 Rock et al.
2016/0076176 A1 3/2016 Rock et al.
2016/0082277 A1 3/2016 Foshee, Jr. et al.
2016/0113581 A1 4/2016 Amir et al.
2016/0256104 A1 9/2016 Romem et al.
2016/0283900 A1 9/2016 Johnson et al.
2017/0014073 A1 1/2017 Shoshani et al.

(56) References Cited

U.S. PATENT DOCUMENTS

2017/0027469 A1 2/2017 Amir et al.
2017/0036066 A1 2/2017 Chahine
2017/0040758 A1 2/2017 Amir et al.
2017/0095175 A1* 4/2017 Allavatam ............. A61B 5/287
2017/0162840 A1 6/2017 Pendry
2017/0319862 A1 11/2017 Foshee, Jr. et al.
2017/0367591 A1 12/2017 Jorgensen
2018/0116537 A1 5/2018 Sullivan et al.
2018/0117299 A1 5/2018 Gustavson et al.
2018/0184933 A1 7/2018 Sullivan et al.
2018/0185662 A1 7/2018 Foshee, Jr. et al.
2018/0243578 A1 8/2018 Volosin
2018/0361165 A1 12/2018 Jaax et al.
2019/0030352 A1 1/2019 Sullivan et al.
2019/0076666 A1 3/2019 Medema
2019/0116896 A1 4/2019 Armour et al.
2019/0321650 A1 10/2019 Raymond et al.
2019/0329052 A1* 10/2019 Kim ....................... A61B 5/318
2021/0178172 A1* 6/2021 Kim ....................... A61B 5/366
2023/0149258 A1* 5/2023 Kaufman ............. A61H 31/005
607/5
2024/0374136 A1* 11/2024 Sørensen ............. A61B 5/0015

FOREIGN PATENT DOCUMENTS

JP 4320257 B2 8/2009
JP 2014526282 A 10/2014
JP 5963767 B2 8/2016
WO 1998/39061 A2 9/1998
WO 2011/146448 A1 11/2011
WO 2012/064604 A1 5/2012
WO 2012/151160 A1 11/2012
WO 2015/056262 A1 4/2015

OTHER PUBLICATIONS

Klein et al., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

ARRHYTHMIA DETECTION IN A WEARABLE MEDICAL SYSTEM

CROSS-REFERENCE TO RELATED APPLICATIONS

This application claims priority to and the benefit of the provisional patent application No. 63/395,282 titled "Asystole Detection in A Wearable Medical Device," filed in the United States Patent and Trademark Office on Aug. 4, 2022. The specification of the above referenced patent application is incorporated herein by reference in its entirety.

TECHNICAL FIELD

The invention relates to a wearable device and more particularly, but not by way of limiting, the invention relates to detecting events related to cardiac arrhythmia.

BACKGROUND

Cardiac rhythm disorders or cardiac conditions occur when electrical signals that coordinate heart's beats are awry or faulty. Such faulty signaling causes the heart to either beat too fast, too slow, or irregularly. The cardiac rhythm disorders corresponding to the faster and slower heart beats are known as tachyarrhythmia and bradyarrhythmia, respectively, and a cardiac rhythm disorder corresponding to a cessation of electrical and mechanical activity of the heart is known as asystole. Further, at least one of the cardiac rhythm disorders can lead to another cardiac rhythm disorder, such as Ventricular Fibrillation (VF), which could result in Sudden Cardiac Arrest (SCA) that endangers the life of a patient. Early detection of the cardiac rhythm disorders can prevent the resultant disastrous situations.

Conventionally, arrhythmia detectors are utilized for detecting the cardiac rhythm disorders such as tachyarrhythmia and bradyarrhythmia. The arrhythmia detectors, such as conventional QRS detectors, are highly sensitive to avoid the risk of missing tachyarrhythmia detection. However, the high sensitivity of a typical conventional QRS detector can increase the risk of incorrectly detecting asystole. Conversely, reducing the sensitivity of the conventional QRS detector or using a less-sensitive conventional QRS detector reduces the risk of incorrectly detecting asystole and/or bradyarrhythmia. However, with the low sensitivity, the conventional QRS detector may detect tachyarrhythmia incorrectly. Further, a single arrhythmia detector or a single sensing mechanism is not sufficient for detecting different arrhythmia conditions and even if the arrhythmia detector detects the cardiac rhythm disorders, other one or more devices are required for providing therapy based on a type of the detected cardiac rhythm disorder.

SUMMARY

The present disclosure relates to a wearable medical system for detecting cardiac arrythmia condition of a patient. In one aspect of the present disclosure, the wearable medical system comprises a support structure, a plurality of ECG electrodes to sense an ECG signal of the patient, and an energy output device to store an electrical charge. The wearable medical system further comprises an output circuit coupled to the energy output device, a plurality of therapy electrodes, and a processor. The plurality of therapy electrodes is coupled to the support structure and the output circuit, and the plurality of therapy electrodes deliver therapy to the patient. The processor is coupled to the plurality of ECG electrodes and the output circuit. The processor comprises a QRS detector module that has a first threshold and a second threshold.

The QRS detector module comprises a first QRS detector that analyzes the ECG signals for the first threshold and a second QRS detector that analyzes the ECG signals for the second threshold. The first threshold is configured to detect tachyarrhythmia and the second threshold is configured to detect bradyarrhythmia. Whenever the first threshold and/or the second threshold is exceeded by the ECG signal, the QRS detector module stores information regarding instances or time-related data. Based on the stored information, heart rate of the patient is determined. Upon identifying a cardiac condition based on the determined heart rate, a defibrillation shock or a pacing pulse is delivered to the patient by the therapy electrodes.

The wearable medical system further comprises a user interface that includes audio and/or visual alarms to alert the user, the patient, or a passerby. The wearable medical system further comprises a band pass filter for filtering the ECG signals.

BRIEF DESCRIPTION OF THE DRAWINGS

The above-mentioned implementations are further described herein with reference to the accompanying figures. It should be noted that the description and figures relate to exemplary implementations and should not be construed as a limitation to the present disclosure. It is also to be understood that various arrangements may be devised that, although not explicitly described or shown herein, embody the principles of the present disclosure. Moreover, all statements herein reciting principles, aspects, and embodiments of the present disclosure, as well as specific examples, are intended to encompass equivalents thereof.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, and the like. In other instances, well-known structures or methods, associated with a wearable medical system, have not been shown or described in detail to avoid unnecessarily obscuring descriptions of the embodiments.

Unless the context indicates otherwise, throughout the specification and claims which follow, the word "comprise" and variations thereof, such as, "comprises" and "comprising" are to be construed in an open, inclusive sense that is as "including, but not limited to." Further, the terms "first,"

"second," and similar indicators of the sequence are to be construed as interchangeable unless the context clearly dictates otherwise.

Reference throughout this specification to "one aspect" or "an aspect" means that a particular feature, structure, or characteristic described in connection with an embodiment is included in at least one aspect. Thus, the appearances of the phrases "in one aspect" or "in an aspect" in various places throughout this specification are not necessarily all referring to the same embodiment. Furthermore, the particular features, structures, or characteristics may be combined in any suitable manner in one or more aspects.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

Figure 1:
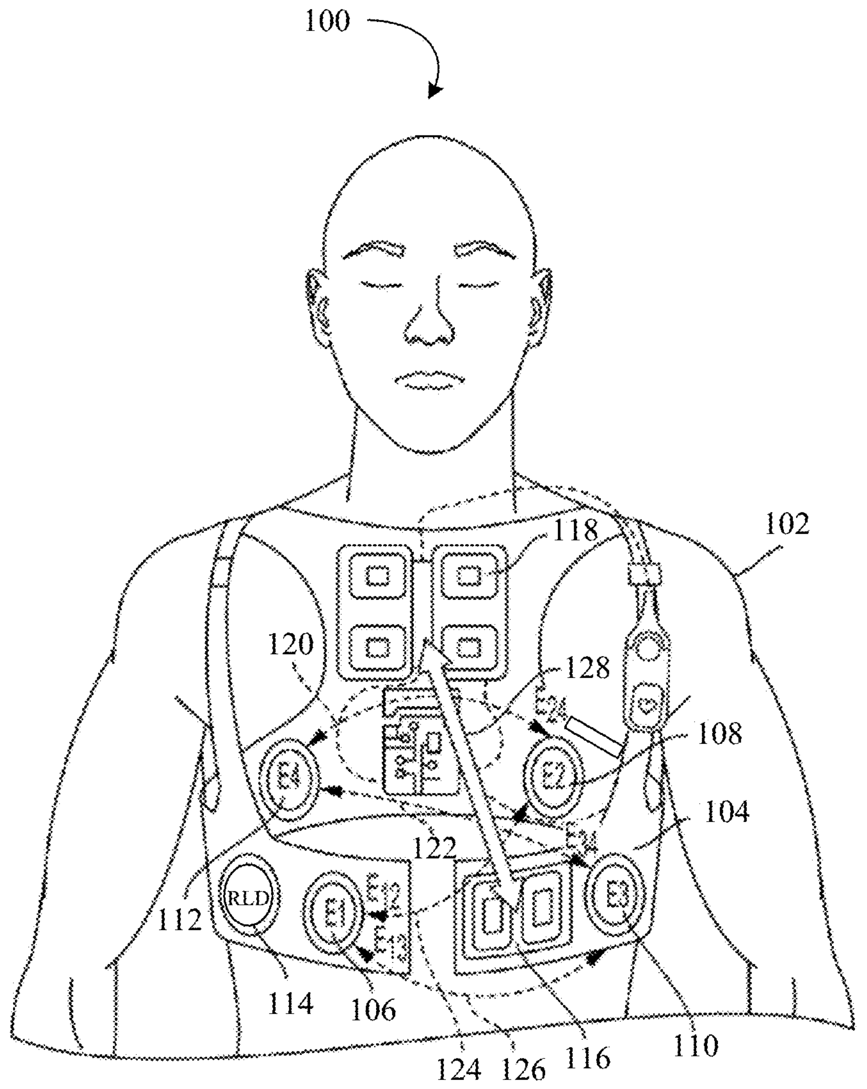
FIG. 1 illustrates an example of a wearable medical system (WMS) worn by a user.

FIG. 1 illustrates an example of a wearable medical system (WMS) 100 worn by a user 102. The WMS 100 at least monitors electrocardiogram (ECG) of the user 102. In an example, the user 102, also referred to as a person 102, is a patient wearing an ECG monitoring device, such as the WMS 100. The patient 102 may be at least one of ambulatory without necessarily being bed-ridden and essentially bed-ridden. In an example, the user 102 may be a clinician including, but not limited to, a doctor, nurse, emergency medical technician (EMT), or other similarly tasked individuals or group of individuals. In an example, the user 102 may be a bystander who might offer assistance or a trained person. In an example, the user 102 may be a remotely located and trained caregiver in communication with the WMS 100. Therefore, the terms "user," "patient," and "bystander" may be used interchangeably throughout the disclosure. The particular context of these and other related terms within this description should be interpreted accordingly.

The WMS 100 includes a support structure 104 or a garment configured to be worn by the user 102 for one or more hours, days, or months. It will be understood that the support structure 104 is shown generically in FIG. 1 and FIG. 1 is provided to illustrate concepts about the support structure 104 and the details disclosed in FIG. 1 are not to be construed as limiting how the support structure 104 is implemented, or how it is worn.

The support structure 104 is implemented in a single component or a combination of multiple components. The support structure 104, in some embodiments, includes a vest, a half-vest, a garment, and the like, that may be worn similarly to analogous articles of clothing. In some embodiments, the support structure 104 includes a harness, one or more belts or straps, and the like, that allows the support structure 104 to be worn by the patient 102 around torso, hips, over the shoulder, and the like. The one or more belts and straps are adjustable based on the physique of the patient 102. In some embodiments, the support structure 104 is waterproof. In some embodiments, the support structure 104 includes a container or housing, allowing the support structure 104 to be worn by the patient 102 using an adhesive material, for example as shown and described in U.S. Pat. No. 8,024,037 which is incorporated herein by reference in its entirety. The support structure 104 may be implemented as support structure described in the U.S. Pat. Publication. No. US2017/0056682 A1, which is incorporated herein by reference in its entirety. The person skilled in the art will recognize that additional components of the WMS 100 may be present in the container of the support structure 104 instead of being attached externally to the support structure 104, for example as described in the aforementioned '682 patent publication.

The support structure 104 comprises a plurality of ECG electrodes positioned on a front portion such as electrodes (E1) 106 and (E2) 108 and on a back portion such as an electrode (E3) 110 to sense ECG signals and an electrode (E4) 112. Additionally, the support structure 104 includes a right-leg drive (RLD) electrode 114, also referred to as a common mode electrode to manage common mode noise. The front portion further includes an anterior defibrillation electrode 116 and the back portion further includes a posterior defibrillation electrode 118. The anterior defibrillation electrode 116 and the posterior defibrillation electrode 118 may be referred to as an anterior defibrillation pad 116 and a posterior defibrillation pad 118, respectively. The anterior defibrillation electrode 116 and the posterior defibrillation electrode 118 are collectively referred to as the defibrillation electrodes 116, 118.

The ECG electrodes (E1-E4), collectively referred to as ECG electrodes 106-112, may be placed circumferentially around the torso of the patient 102 so that the support structure 104 may be used to ensure adequate electrode-skin contact with the skin of the patient 102. It should be noted that alternative placement of ECG electrodes 106-112 may be used, and the scope of the disclosed subject matter is not limited in this respect. For example, adhesive electrode embodiments may provide flexibility in electrode placement in selected locations of the body of the patient 102 and may achieve better signal pickup at the selected locations. For example, locations of the ECG electrodes 106-112 may be selected during a patient-fitting process in which various locations can be changed, and locations with better or the best ECG signals can be selected, although the scope of the disclosed subject matter is not limited in this respect.

The ECG electrodes 106-112 may couple with a cardiac monitoring system or a device that includes a wearable cardioverter defibrillator (WCD) or a wearable cardiac monitor (WCM). In some embodiments, the WMS 100 includes the cardiac monitoring system. The WCM is configured to continuously monitor the ECG signals of the patient 102 and generate a rhythm discrimination. In some embodiments, the WCM is configured to obtain the ECG signals of the patient 102. The ECG signals may be digitized by the WCM for digital processing.

In an example, four differential vectors may be formed by subtracting two digitized ECG signals. An ECG rhythm analysis may then be performed on the four differential vectors. The differential vectors include, for example, a vector (E24) 120, a vector (E34) 122, a vector (E12) 124, and a vector (E13) 126 that are derived from single-ended vectors. The WMS 100 may generate a defibrillator shock vector 128 between the anterior defibrillation electrode 116 and the posterior defibrillation electrode 118.

In some embodiments, the ECG signals from the four ECG electrodes 106-112, may be combined to form six different vectors. In some embodiments, the ECG monitoring device, such as the WMS 100, may use the four vectors i.e., E24 120, E34 122, E12 124, and E13 126, for QRS complex analysis or heart rate analysis to determine if a shock should be applied. Thus, the WMS 100 is capable of performing synchronous cardioversion as a therapy based on the heart rate analysis. In some embodiments, the WMS 100 is capable of performing the heart rate analysis and shock application determination if one or more of the above-mentioned vectors E24 120, E34 122, E12 124, and E13 126 are noisy or one or more of the ECG electrodes 106-112 or ECG leads are in a lead-off condition. The lead-off condition is a resultant of the ECG lead or at least one of the ECG electrodes 106-112 or the defibrillation electrodes 116, 118 not contacting the skin of the patient 102 or not sufficiently contacting the skin of the patient 102.

In some embodiments, at least three ECG electrodes of the ECG electrodes 106-112 may be used and corresponding three ECG vectors of the ECG vectors E24 120, E34 122, E12 124, and E13 126 may be analyzed. In some embodiments, five or six ECG vectors may be analyzed using all the ECG electrodes 106-112. In some embodiments, a single vector may be used and analyzed. It should be noted that, in general, the WMS 100 or the ECG monitoring device may use and analyze fewer than four vectors or greater than four vectors, and the number of vectors may be increased beyond six vectors by using additional ECG electrodes, and the scope of the disclosed subject matter is not limited in this respect. In some embodiments, the WMS 100 or the ECG monitoring device may use four channels out of six possible differential channels formed from four independent electrodes placed around the chest of the patient 102. In some embodiments, the WMS 100 may use a different number of channels, including only one channel. In some embodiments, the WMS 100 may use a QRS detector of a single channel or multiple channels filtered ECG signal to detect a possible arrhythmia for full rhythm analysis. In some embodiments, where the ECG monitoring device comprises the WMS 100, a different number of ECG electrodes may be used, often a reduced number of electrodes or a different garment system may be used other than the support structure 104. In some embodiments, the ECG electrodes 106-112 may provide multiple vectors of the ECG signal and the QRS detector may operate on each of the multiple vectors.

The WMS 100, for example, is capable of excluding one or more of the vectors E24 120, E34 122, E12 124, and E13 126 that have noise or when a lead-off condition is detected. Monitoring four vectors rather than monitoring two vectors is believed to contribute to enhanced ECG signal analysis and processing of a shock application algorithm to reduce the number of false shock events.

In some embodiments, the WMS 100 is referred to as a cardiac monitoring device that uses the ECG electrodes 106-112 which may be configured to detect QRS complexes similar to QRS complexes that are normally conducted through an atrioventricular (AV) node. The QRS complexes conducted through the AV node can be referred to herein as "normally conducted QRS complexes." Since the ECG signals can be a mixture of multiple different QRS morphologies, normally conducted QRS complex identification may be used as described herein to determine the rhythms more accurately, including but not limited to, determining atrial fibrillation (AF) and the associated heart rate (HR) and HR variability, according to one or more embodiments. In some embodiments, the WMS 100 may detect the ECG signals from the ECG electrodes 106-112 and may not provide therapy, such as the application of shock or providing pacing pulses using the defibrillation electrodes 116, 118, also referred to as therapy electrodes 116, 118.

Figure 2:
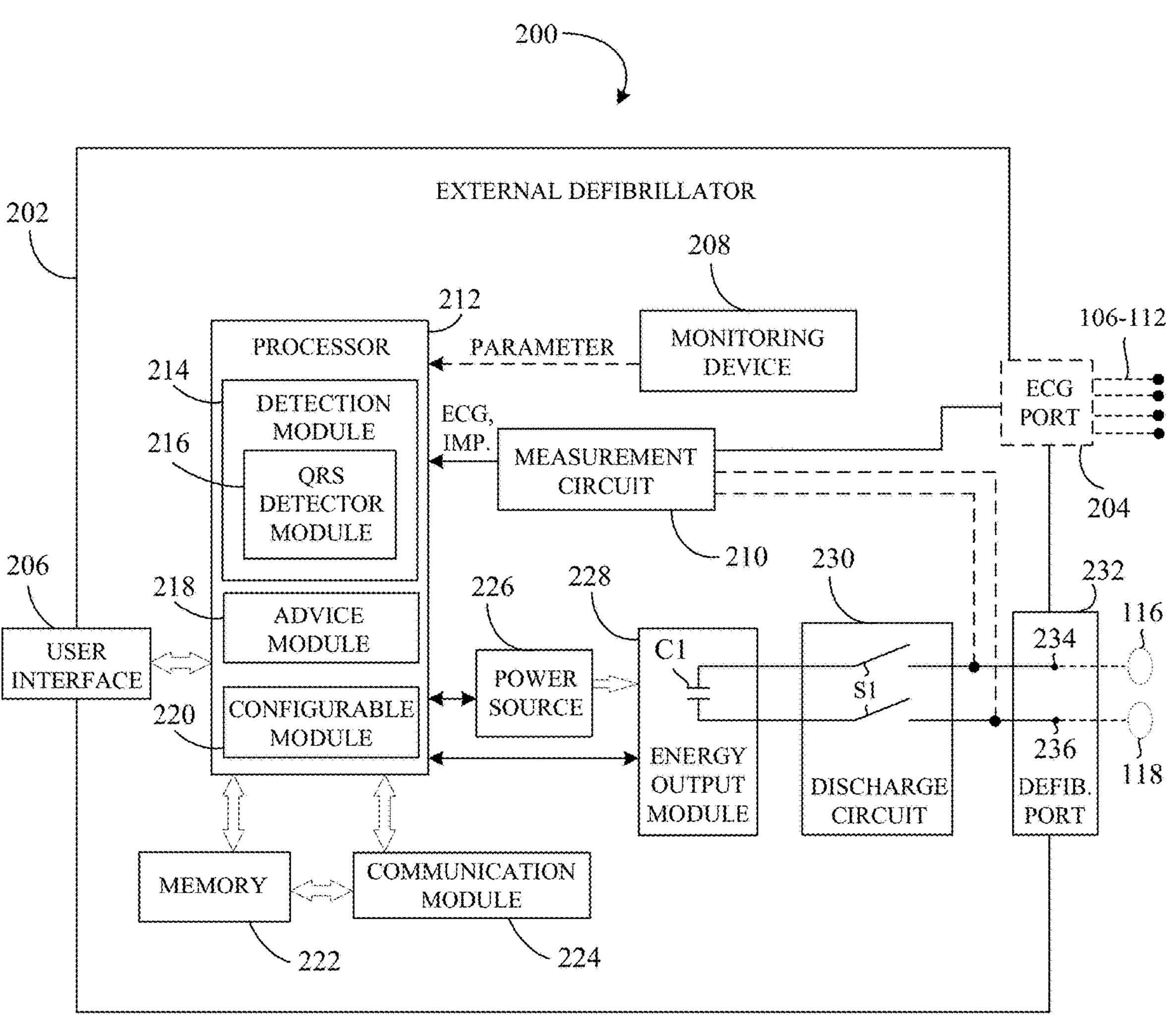
FIG. 2 illustrates a block diagram of the wearable medical system.

FIG. 2 illustrates an external defibrillator 200 coupled to the WMS 100, as described in FIG. 1. The external defibrillator 200 is capable of detecting and determining cardiac rhythm disorders and providing therapy based on the determination of the cardiac rhythm disorders. One or more components of the external defibrillator 200 are provided in housing 202, which is also referred to as a casing 202. The housing 202, in some embodiments, is the container described in FIG. 1. The components of the external defibrillator 200, in some embodiments, include an ECG port 204, a user interface 206, a monitoring device 208, a measurement circuit 210, a processor 212, a memory 222, a communication module 224, a power source 226, an energy output module 228, a discharge circuit 230, and a defibrillation port 232 coupled to the defibrillation electrodes 116, 118. The terms "external defibrillator" and "wearable medical system (WMS)," are interchangeably used, unless the context clearly dictates otherwise.

The user interface 206 may include one or more output devices, which may be visual, audible, or tactile, for communicating with the user 102, such as the bystander or physician, or providing human-perceptible indications (HPIs) by outputting images, sounds, vibrations, and the like. One of the one or more output devices further includes, for example, a light to indicate or a screen to display sensed, detected, and/or measured information by the external defibrillator 200 and/or the ECG electrodes 106-112, as disclosed in FIG. 1, and provide visual feedback to a rescuer for resuscitation attempts of the patient 102, as disclosed in FIG. 1. One of the one or more output devices, for an example, may be a speaker, which could be configured to issue voice prompts, beeps, loud alarm sounds, and/or words to warn bystanders, and the like.

The user interface 206 may further include one or more input devices for receiving inputs from the users. The one or more input devices may include various controls, such as push buttons, keyboards, touchscreens, one or more microphones, and the like. One of the one or more input devices may be a cancel switch, which is sometimes called an "I am alive" switch or "live man" switch because actuating the cancel switch by the patient 102 can prevent impending delivery of a shock to the patient 102.

The ECG port 204, also referred to as a sensor port 204, is coupled to or adapted for plugging in the ECG electrodes 106-112, also known as sensing electrodes 106-112 or the ECG leads. The ECG electrodes 106-112, in an example, may be connected continuously to the ECG port 204. The external defibrillator 200 may receive inputs from the ECG electrodes 106-112 through the ECG port 204. The ECG electrodes 106-112 are types of transducers that can sense an ECG signal, for example, a 12-lead signal. In some embodiments, the ECG electrodes 106-112 can sense a signal from a different number of leads, especially if the ECG electrodes 106-112 make good electrical contact with the body of the patient 102 and particularly with the skin of the patient 102. The ECG electrodes 106-112 can be attached to the inside of the support structure 104, as disclosed in FIG. 1, for making good electrical contact with the patient 102.

The defibrillation port 232, in some embodiments, may be a socket in the housing 202. The defibrillation port 232 may include electrical nodes 234, 236. Leads of the defibrillation electrodes 116, 118 may be plugged into the defibrillation port 232, to make electrical contact with electrical nodes 234, 236, respectively. In some embodiments, the defibrillation electrodes 116, 118 are connected continuously to the defibrillation port 232. The defibrillation port 232 may be used for guiding, via the defibrillation electrodes 116, 118, to the patient 102 at least some of electrical charge stored in the energy output module 228. The electric charge applied to the patient 102 is the shock for purpose of defibrillation, pacing, and the like. The defibrillation electrodes 116, 118 may be attached to the inside of the support structure 104 for making good electrical contact with the patient 102.

The external defibrillator 200, according to some embodiments, also includes a fluid that can be deployed automatically between the ECG electrodes 106-112 and the skin of the patient 102. The fluid may be conductive, such as by including an electrolyte, for establishing better electrical contact between the ECG electrodes 106-112 and the skin of the patient 102. When the fluid is deployed, the electrical impedance between the ECG electrodes 106-112 and the skin is reduced. The fluid may be in the form of a low-viscosity gel that does not flow away from the ECG electrodes 106-112 after the fluid has been deployed. The fluid can be used for both the defibrillation electrodes 116, 118, and the ECG electrodes 106-112.

The fluid may be initially stored in a fluid reservoir (not shown in FIG. 2), coupled to the support structure 104, as disclosed in FIG. 1. Additionally, the external defibrillator 200, in an example, further includes a fluid deploying mechanism (not shown). The fluid deploying mechanism may be configured to cause at least some of the fluid to be released from the fluid reservoir and be deployed near one or more locations to which the ECG electrodes 106-112 are configured to be attached to the patient 102. In some embodiments, the fluid deploying mechanism is activated prior to the application of the shock, responsive to receiving an activation signal from the processor 212.

The monitoring device 208 is also referred to as an internal monitoring device 208 since the monitoring device 208 is incorporated within the housing 202. The monitoring device 208 may sense or monitor patient parameters such as physiological parameters of the patient 102, state parameters of the patient 102, system parameters, and/or environmental parameters, all of which can be called patient data. In an example, the monitoring device 208 may include or be coupled to one or more sensors to sense the patient data.

The physiological parameters of the patient 102, for example, and without limitation, include data related to one or more physiological parameters, also referred to as physiological parameters data, that can assist the external defibrillator 200 in detecting whether or not the patient 102 needs a shock or other intervention or assistance. The physiological parameters data may also, in an example, include medical history of the patient 102, event history, and the like. The physiological parameters data further includes ECG, blood oxygen level, blood flow, blood pressure, blood perfusion, pulsatile change in light transmission or reflection properties of perfused tissue, heart sounds, heart wall motion, breathing sounds, and the pulse of the patient 102.

Accordingly, the monitoring device 208 includes one or more sensors configured to acquire physiological signals of the patient 102. In some embodiments, the one or more sensors or transducers may include the one or more ECG electrodes 106-112 to detect or obtain the ECG signals, a perfusion sensor, a pulse oximeter, a device for detecting blood flow, for example, a Doppler device, and the like. In some embodiments, the one or more sensors include a sensor for detecting blood pressure, for example, a cuff, an optical sensor, illumination detectors, and sensors perhaps working together with light sources for detecting color change in tissue. In some embodiments, the one or more sensors include a motion sensor, a device that can detect heart wall movement, a sound sensor, a device with a microphone, a SpO2 sensor, and the like. In view of the foregoing, it will be appreciated that such sensors can help detect pulse of the patient 102, and can therefore also be called pulse detection sensors, pulse sensors, and pulse rate sensors. In addition, a person skilled in the art may implement other ways of performing pulse detection.

In some embodiments, the monitoring device 208 and/or the processor 212 may detect a trend in the monitored physiological parameters data of the patient 102. The trend may be detected by comparing values of parameters at different times over short and/or long terms. The physiological parameters, whose detected trends may help a cardiac rehabilitation program, include a) cardiac function, for example, ejection fraction, stroke volume, cardiac output, and the like; b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above; f) respiratory function, respiratory rate, and the like; g) motion, level of activity; and the like.

The detected trend may be stored and/or reported to a physician via one or more wired or wireless communication links, along with a warning to the physician monitoring progress or health status of the patient 102, if warranted. The reported trends provide clarity and updated information corresponding to the patient 102, to the physician. The physician may gauge if a condition is either not improving or deteriorating based on the reported trends.

The state parameters include recorded aspects of the patient 102, such as motion, posture, whether the patient 102 has spoken or communicated with a physician recently along with what has been spoken, and the like. In an example, the state parameters further include a history of the state parameters. In an example, the monitoring device 208 may include a location sensor such as a Global Positioning System (GPS) location sensor. The location sensor may detect the location of the patient 102, and speed can be detected as a rate of change of location over time.

In some embodiments, the monitoring device 208 may include motion detectors that can be configured to detect a motion event and output a motion signal indicative of motion of the motion detector, and thus motion of the patient 102. The state parameters can assist in narrowing down the determination of whether Sudden Cardiac Arrest (SCA) is indeed occurring. In some embodiments, the external defibrillator 200 includes a motion detector. The motion detector can be made in many ways as is known in the art, for example by using an accelerometer. The motion event can be defined as convenient, for example, a change in motion from a baseline motion or rest, and the like. In response to the detected motion event, the motion detector may render or generate a motion detection input that may be received by a subsequent device or functionality. In some embodiments, the WMS 100 may include a motion detector coupled to the external defibrillator 200.

The system parameters may include system identification, battery status, system date and time, reports of self-testing, records of data entered, records of episodes and interventions, and the like. The environmental parameters may include ambient temperature and pressure. Moreover, a humidity sensor may provide information as to whether or not it is likely raining. The detected location of the patient 102 may also be considered as one of the environmental parameters. The patient location may be presumed if the monitoring device 208 includes the GPS location sensor as mentioned above, and if the patient 102 is wearing the WMS 100.

The external defibrillator 200 also includes the measurement circuit 210 communicatively coupled to the monitoring device 208 and the one or more sensors or transducers. The measurement circuit 210 senses one or more electrical physiological signals of the patient 102 from the sensor port 204. In an embodiment, if the external defibrillator 200 lacks the sensor port 204, the measurement circuit 210 may, in an example, obtain physiological signals through the electrical nodes 234, 236 instead, when the defibrillation electrodes 116, 118 are attached to the patient 102. The input to the measurement circuit 210 through the electrical nodes 234 and 236 is the ECG signal that reflects the ECG measurement. The patient data, in an example, is the ECG signal that may be sensed as a voltage difference between the defibrillation electrodes 116, 118. In addition, the patient parameter may be an impedance, which can be sensed between the defibrillation electrodes 116, 118 and/or between the connections of the sensor port 204 considered pairwise.

Sensing the impedance may be useful for detecting, among other things, whether the defibrillation electrodes 116, 118 and/or the ECG electrodes 106-112 are not making good electrical contact with the body of the patient 102. The physiological signals of the patient 102 may be sensed when available. The measurement circuit 210 can render or generate information about the physiological signals of the patient 102 as inputs, data, other signals, and the like. As such, the measurement circuit 210 may be configured to render a patient input responsive to the patient parameters sensed by a sensor. In some embodiments, the measurement circuit 210 may be configured to render the patient input, such as values of the ECG signal, responsive to the ECG signal sensed by the ECG electrodes 106-112. Although the information rendered by the measurement circuit 210 is output from it, the information may be called an input because the information is received as an input by a subsequent device or functionality.

The external defibrillator 200 also includes the processor 212 which may be implemented in different ways in various embodiments. The different ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination thereof, and the like.

The processor 212 may include, or have access to, a non-transitory storage medium, such as the memory 222 that, in some embodiments, is a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, instances of the software may be referred to as a "module" and by other similar terms. However, the term "module" used in the context of disclosure is intended to be broad and may include hardware, software, distributed components, remote components (e.g., cloud computing), and the like. Further, a module includes a set of the instructions so as to offer or to fulfill a particular functionality and the processor 212 includes one or more modules. Embodiments of modules and the functionality delivered are not limited by the embodiments described in this document.

In some embodiments, the processor 212 includes a detection module 214, an advice module 218, and a configurable module 220. The detection module 214, in an example, includes a QRS detector module 216. The QRS detector module 216 is a QRS detector that continuously monitors the ECG signals of the patient 102 wearing the WMS 100 for the purposes of arrhythmia detection. The QRS detector module 216 is similar to the QRS detector described in FIG. 1. The QRS detector module 216, in some embodiments, detects QRS complexes in real-time ECG signals. The QRS detector module 216, in some embodiments, detects QRS complexes in previously obtained and stored ECG signals. For example, in some embodiments, multiple segments of data from the received ECG signals may be accumulated and then processed by the QRS detector module 216 similar to QRS detectors that utilize the real-time ECG signal. The QRS detector module 216 uses the detected QRS complexes for determining average heart rate and QRS widths. Such embodiments may be advantageously used when the conventional medical device does not provide pacing therapy.

The QRS detector module 216 is configured to process the ECG signal of a differential vector to detect a possible arrhythmia. In some embodiments, the ECG signal is filtered, for example, using a band pass filter, before being processed by the QRS detector module 216. In an embodiment that includes multiple vectors, such as the ECG vectors 120, 122, 124, and 126, as described in FIG. 1, the QRS detector module 216 may process each of the ECG vectors 120, 122, 124, and 126.

The QRS detector module 216 may utilize a dual detection scheme that uses a more sensitive threshold to detect a tachyarrhythmia condition and a less sensitive threshold to detect a bradyarrhythmia and/or asystole condition. As an example, a first threshold is configured to detect the tachyarrhythmia condition and a second threshold is configured to detect the bradyarrhythmia condition. The QRS detector module 216, in some embodiments, includes a QRS detector for tachyarrhythmia detection and a different QRS detector for bradyarrhythmia and/or asystole detection. The QRS complexes detected by the QRS detector module 216 may be used to determine the heart rate (e.g., the inverse of the R-R interval of consecutive QRS complexes), and the width of each of the detected QRS complexes. In some embodiments, the QRS detector module 216 calculates the heart rate using the inverse of the R-R interval of the ECG signals exceeding the first threshold and a recalculated first threshold or exceeding the second threshold and a recalculated second threshold. Thus, a single QRS detector module 216 is capable of detecting different cardiac conditions or cardiac rhythm disorders using a common ECG signal for the detection.

In some embodiments, the detected information or parameters may be used in rhythm analysis algorithms such as described in U.S. Pat. No. 9,592,403, issued on May 14, 2017, entitled "Wearable cardioverter defibrillator (WCD) system making shock/no shock determinations from multiple patient parameters" and/or U.S. Pat. No. 9,757,579, issued on Sep. 12, 2017, entitled "Wearable cardioverter defibrillator (WCD) system informing patient that it is validating just-detected cardiac arrhythmia." Embodiments of the QRS detector module 216 are described below in conjunction with FIGS. 3-5.

In an embodiment, the detection module 214 includes a Ventricular Fibrillation (VF) detector. The ECG signal sensed through the ECG electrodes 106-112 is received as data by the detection module 214 from the measurement circuit 210. The data to the detection module 214 may be available as inputs, data that reflects values, or values of other signals. The data may be used by the VF detector to determine whether the patient 102 is experiencing VF. Detecting the VF is useful because the VF typically results in the SCA. The detection module 214 may also include a Ventricular Tachycardia (VT) detector, and the like.

The advice module 218 may receive an output of the detection module 214 and generate advice for the one or more components of the external defibrillator 200 regarding a subsequent course of action. The advice module 218 may provide a variety of advice based on the output of the detection module 214. In some embodiments, the advice is a shock or no shock determination that the processor 212 can make via the advice module 218. The shock or no shock determination may be made by executing a stored shock advisory algorithm. The shock advisory algorithm can make a shock or no shock determination from the ECG signals that are captured according to embodiments and determine whether or not a shock criterion is met. Further, the QRS detector module 216 may be adaptive and track the trends or tendencies of the heart rate of the patient 102 along with the patient parameters which may be considered for the shock or no shock determination.

For example, in some embodiments, the processor 212 may make the shock or no shock determinations using the rhythm analysis algorithms as described in the aforementioned '403 and '579 patents. The example rhythm analyses may use the heart rates and/or the QRS widths determined from the ECG signals of the patient 102 as received from the detection module 214. The determination may be made from the rhythm analysis of the ECG signal or otherwise.

In some embodiments, when the determination is to shock, the ECG electrodes 106-112, coupled to the defibrillation port 232, deliver the electrical charge to the patient 102. Delivering the electrical charge is also known as discharging and shocking the patient 102 for defibrillation, pacing, and the like. In ideal conditions, a reliable shock or no shock determination may be made by analyzing a segment of the ECG signal of the patient 102. In practice, however, the ECG signal is often corrupted by electrical noise, which reduces accuracy of the analyses of the ECG signal and results in an incorrect detection of heart arrhythmia or the cardiac rhythm disorder, which further results in a false alarm to the patient 102. Noisy ECG signals may be handled as described in U.S. patent application Ser. No. 16/037,990, filed on Jul. 17, 2018, and published as US 2019/0030351 A1, and also in U.S. patent application Ser. No. 16/038,007, filed on Jul. 17, 2018, and published as US 2019/0030352 A1, both by the same applicant and incorporated herein by reference. The ECG signal may be processed accordingly to eliminate noise or other unnecessary artifacts to avoid the incorrect detection of the heart arrhythmia.

In some embodiments, the QRS detector module 216 detects the ECG signals from multiple channels such as the six possible differential channels. The QRS detector module 216 may apply a voting scheme to the multiple channels that are time-synchronized to determine if a QRS complex was detected. For example, in a four-channel system, if the QRS detector module 216 detects one or more QRS complexes in at least three of the four channels, the voting scheme may output a result that a QRS complex was detected. The detection of the QRS complexes allows R-wave in the detected one or more QRS complexes to be used in the heart rate calculation. However, if only one or two channels of the four-channel system detect a QRS complex, the QRS detector module 216 assumes that artifacts detected are noise and not the actual QRS complex.

In some embodiments, multiple channels are considered for the heart rate calculation and each channel of the multiple channels is coupled to a dedicated QRS detector module. In an example, the external defibrillator 200 assumes that one or more channels of the multiple channels are noisy and remaining channels of the multiple channels are not noisy. The QRS detector modules coupled to the one or more noisy channels perform false QRS detection with shorter R-R interval based on which the heart rate is determined to be high. A channel, of the remaining channels, with lowest heart rate represents a noise free or lowest noise channel. For example, to detect VT, if a lowest heart rate>(VT rate−Δ), then a segment-based rhythm analysis is applied, where Δ may be about 20 bpm as an example.

The external defibrillator 200 is capable of providing a varied intensity of shock after determining that a shock is necessary. The external defibrillator 200 provides a defibrillation shock to the patient 102 upon determining the tachyarrhythmia condition and delivers pacing pulses, with an intensity lower than defibrillation shock, to the patient 102 upon determining the bradyarrhythmia or asystole condition.

The processor 212 may include additional modules, such as the configurable module 220 that, in some embodiments, is specifically coupled to an accelerometer. Several movements of the patient 102 may result in a higher heart rate which may be erroneously considered as the tachyarrhythmia condition, thereby providing the defibrillation shock. By utilizing the accelerometer and the configurable module 220 specifically coupled to the accelerometer, the external defibrillator 200 may determine the current status of the patient 102 with lesser delay and deliver the defibrillation shock or the pacing pulses accordingly with an increased level of accuracy.

The external defibrillator 200 includes the communication module 224 for establishing the one or more wired or wireless communication links with other devices of other entities, such as a remote assistance center, Emergency Medical Services (EMS), and the like. The communication links may be used to transfer data and commands. The data may be patient data, event information, therapy attempted, Cardiopulmonary resuscitation (CPR) performance, system data, environmental data, and so on. For example, the communication module 224 may wirelessly transmit heart rate, respiratory rate, and other vital signs data daily to a server accessible over the internet, for instance as described in U.S. Pat. Publication No. US 2014/0043149 A1.

The physician of the patient 102 may directly analyze the communicated data or the communicated data may also be analyzed automatically by algorithms designed to detect a developing illness and then notify medical personnel via text, email, phone, and the like. The communication module 224 may also include interconnected sub-components which may be deemed necessary by a person skilled in the art, for example but not limited to, an antenna, portions of the processor 212, supporting electronics, outlet for a telephone or a network cable, and the like.

The external defibrillator 200 also includes the power source 226. To enable portability of the external defibrillator 200, the power source 226, in some embodiments, includes a battery. The battery, in an example, is a battery pack, which may either be rechargeable or non-rechargeable. In an example, a combination of both the rechargeable and the non-rechargeable battery packs is used. An embodiment of the power source 226 may include an alternate current (AC) power override, for where AC power will be available, an energy-storing capacitor, and so on. Appropriate components may be included to provide for charging or replacing the power source 226. In some embodiments, the power source 226 is controlled and/or monitored by the processor 212.

The external defibrillator 200 further may include the energy output module 228, also referred to as an energy output device 228. The energy output module 228 may be coupled to the support structure 104 of the WMS 100, for example, either directly or via the defibrillation electrodes 116, 118 and respective leads. The energy output module 228 temporarily stores electrical energy as an electrical charge, when preparing for discharge of the electrical charge to administer the shock to the patient 102. In some embodiments, the energy output module 228 may be charged from the power source 226 to the desired amount of energy, as controlled by the processor 212. The energy output module 228 includes a capacitor C1, which may be a single capacitor or a system of capacitors, and the like. In some embodiments, the energy output module 228 includes a device that exhibits high power density, such as an ultracapacitor. As described above, the capacitor C1 stores the energy in the form of an electrical charge, for delivering the shock to the patient 102. In some embodiments, the energy output device 228 is a current source device that provides pacing pulses without storing charge.

A decision to deliver a shock may be made responsive to the shock criterion being met. When the decision is to deliver the shock, the processor 212 may be configured to cause at least some or all of the electrical charge stored in the energy output module 228 to be discharged through the patient 102 while the support structure 104 is worn by the patient 102, to deliver the shock to the patient 102.

For causing the discharge, the external defibrillator 200 includes the discharge circuit 230. When the decision is to deliver the shock, the processor 212 may be configured to control the discharge circuit 230 to discharge through the patient 102 at least some of or all of the electrical charge stored in the energy output module 228. The discharging may be performed to the electrical nodes 234, 236, and then to the defibrillation electrodes 116, 118, for causing the shock to be delivered to the patient 102. A time waveform of the discharge may be controlled by controlling the discharge circuit 230. The amount of energy of the discharge may be controlled by how much the energy output module 228 has been charged, and also by how long the discharge circuit 230 is controlled to remain open. The discharge circuit 230, in an example, includes one or more switches S1. The switches S1 may be made or arranged in a number of ways, such as by an H-bridge, and the like. The discharge circuit 230 may also be controlled via the processor 212 and/or the user interface 206.

The external defibrillator 200 further includes the memory 222, which is communicatively coupled with the processor 212. The memory 222 may be implemented in a number of ways, such as but not limited to, volatile memories, Non-Volatile Memories (NVM), Read-Only Memories (ROM), Random Access Memories (RAM), magnetic disk storage media, optical storage media, smart cards, flash memory devices, any combination thereof, and the like. The memory 222 is, thus, a non-transitory storage medium that may include programs for the processor 212, which the processor 212 may be able to read and execute. More particularly, the programs may include sets of instructions in the form of code, which the processor 212 may be able to execute upon reading. The programs may also include other information such as configuration data, profiles, scheduling, and the like that may be acted upon by the instructions. The execution is performed by physical manipulations of physical quantities and may result in functions, operations, processes, acts, actions and/or methods to be performed. In some embodiments, the processor 212 is configured to cause other devices, components, or blocks to perform functions, operations, processes, acts, actions and/or methods mentioned above. The programs may be operational for the inherent needs of the processor 212 and may also include protocols to assist the advice module 218 in decision-making.

The non-transitory computer-readable storage medium is encoded or configured to store computer program instructions, which are QRS detection instructions, defined by modules, for example, 206, 208, 210, 212, 214, 216, 218, 220, 224, and the like, which when executed by a computing device, such as the external defibrillator 200 or the processor 212, cause the computing device to perform operations for identifying the cardiac condition in the patient 102. The operations include detecting the ECG signal using one or more ECG electrodes 106-112. The operations further include activating the QRS detector module 216 for analyzing the ECG signal. The QRS detector module 216 includes two thresholds, the first threshold and the second threshold for analyzing the ECG signal and determining if the ECG signal exceeds the first threshold or the second threshold. The operations corresponding to activating the QRS detector module 216 further include identifying or detecting a sensed event when the ECG signal exceeds the first threshold or the second threshold, and observing a refractory period after the sensed event is detected. The operations corresponding to activating the QRS detector module 216 further include inhibiting identification or detection of a new sensed event during the refractory period.

The operations corresponding to activating the QRS detector module 216 further include measuring a maximum absolute ECG signal amplitude during the refractory period and recalculating the first threshold or the second threshold based on the maximum absolute ECG signal amplitude during the refractory period. The operations further include decreasing at least one of the recalculated first threshold or the recalculated second threshold with time in an exponential manner until the recalculated first threshold or the recalculated second threshold reaches a minimum threshold level. The first threshold and the second threshold are utilized, measured, and set without interaction between the first detector and the second detector. Further, the threshold corresponding to the first or second QRS detector that has detected the cardiac rhythm disorder, is recalculated without necessarily setting the refractory period and recalculating other threshold corresponding to the first or second QRS detector that has not detected the cardiac rhythm disorder. For example, the first QRS detector detects the cardiac rhythm disorder using the first threshold and recalculates and sets the first threshold after the refractory period. However, the second detector does not detect any cardiac rhythm disorder and hence does not recalculate and set the second threshold.

The operations for identifying the cardiac condition in the patient 102 after activating the QRS detector module 216, further include detecting a subsequent ECG signal after the refractory period using the ECG electrodes 106-112. Further, the operations include reactivating the QRS detector module 216 to determine if the subsequent ECG signal exceeds the recalculated first threshold or the recalculated second threshold. In some embodiments, the ECG signal and the subsequent ECG signal are detected on same ECG vector, such as one of the ECG vectors 120, 122, 124, and 126. However, the ECG signal and the subsequent ECG signal may be detected at varied time instances.

The operation includes controlling an output circuit such as the discharge circuit 230, and the energy output module 228 to deliver the defibrillation shock to the patient 102 through the therapy electrodes 116, 118, if the presence of the tachyarrhythmia condition is determined. Further, the operation includes controlling an output circuit such as the discharge circuit 230, and the energy output module 228 to deliver the pacing pulse to the patient 102 through the therapy electrodes 116, 118, if the presence of bradyarrhythmia condition is determined. In some embodiments, the therapy, such as the defibrillation shock and pacing pulse delivery, is provided to the patient 102 depending on which threshold, among the first threshold and the second threshold, was detected to be exceeded by the ECG signal.

In addition, the memory 222 may be configured to store prompts for the user 102 if the user 102 is a local rescuer at a scene where the patient 102 requires any support or interference from the local rescuer. Moreover, the memory 222 may store data including patient data, system data, and environmental data, for example, as received by the monitoring device 208. The data may be stored in the memory 222 before it is transmitted out of the external defibrillator 200. Alternatively, or additionally, the data may be stored in the memory 222 after it is received by the external defibrillator 200.

Figure 3:
FIG. 3 illustrates a QRS detection graph.
Figure 3:
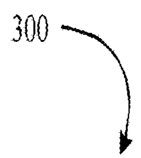
Figure 3:
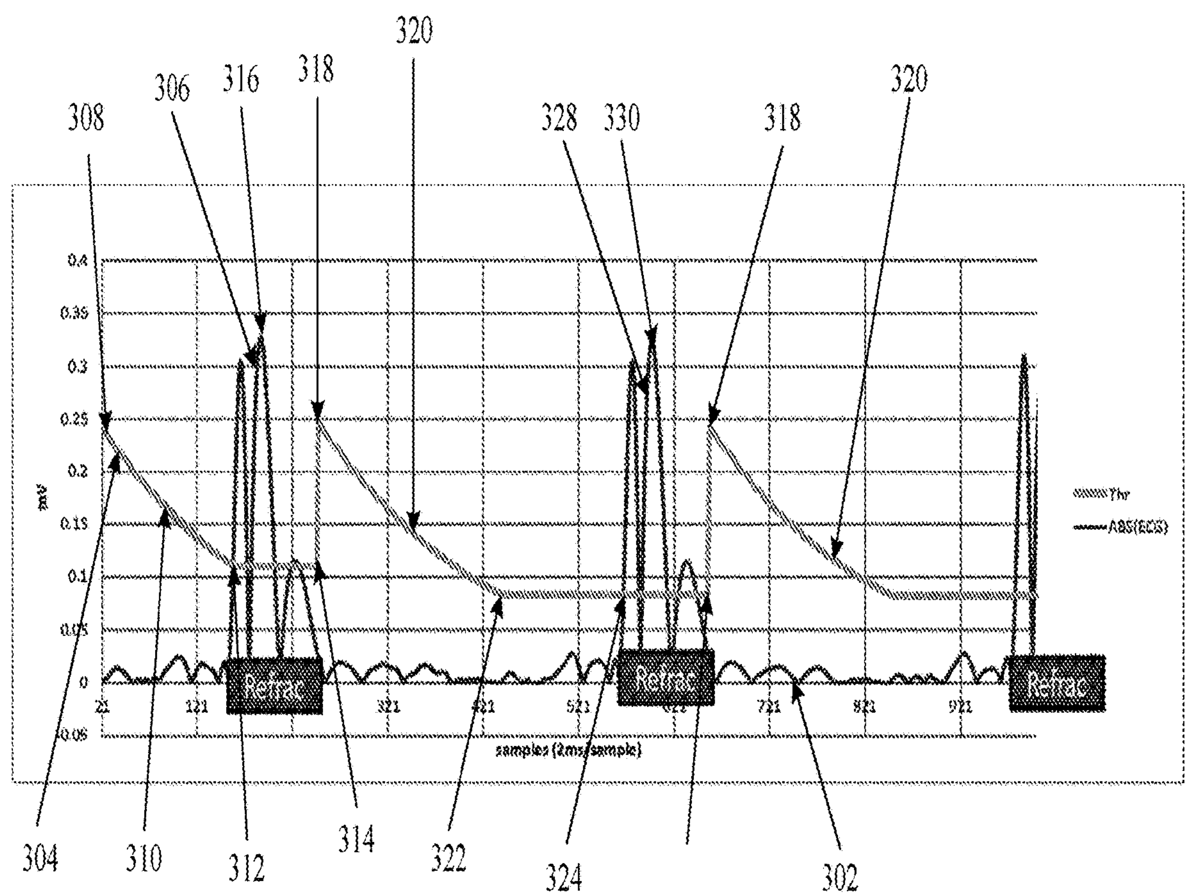

FIG. 3 illustrates a QRS detection graph 300 that includes an ECG signal 302, similar to the ECG signals received from the ECG electrodes 106-112, as disclosed in FIG. 2, in contact with the patient 102. The ECG signal 302, in some embodiments, is received in real-time. The ECG signal 302, in some other embodiments, is received from a database or a storage component. The QRS detection graph 300 is a time versus millivolt graph on which the ECG signal 302 from the ECG electrodes 106-112 is plotted. In some embodiments, the ECG signal 302 is received from the defibrillation electrodes 116, 118. In an example, the ECG signal 302 is rectified. The QRS detection graph 300 further includes a dual detection threshold which is a time-varying threshold. In some embodiments, the dual detection threshold is positioned corresponding to the received ECG signal 302 and set to an initial default value at an initial position 308. The value of the dual detection threshold varies along with time in the time versus millivolt graph. The QRS detector module 216, as disclosed in FIG. 2, utilizes the dual detection threshold for detecting a QRS complex 306 in the received ECG signal 302.

The QRS detector module 216, in some embodiments, includes real-time QRS detectors such as a tachyarrhythmia QRS detector for the tachyarrhythmia detection and a bradyarrhythmia/asystole QRS detector for bradyarrhythmia/asystole detection. The tachyarrhythmia QRS detector is referred to as a first QRS detector hereinafter and the bradyarrhythmia/asystole QRS detector is referred to as a second QRS detector hereinafter. Each of the first and second QRS detectors and the QRS detector module 216 may be implemented in software or as software modules and may execute and run substantially concurrently. The QRS detector module 216 may select a single ECG vector based on a vector selection algorithm and may utilize the selected single ECG vector for detecting the cardiac rhythm disorder. In some embodiments, the QRS detector module 216 may utilize a single channel i.e., differential vector, of the multiple channels available for usage. The channel for the QRS detector module 216 may be determined by the rhythm analysis algorithm, for example as shown and described in U.S. Pat. No. 10,940,323, issued on Mar. 9, 2021, entitled "Wearable Cardioverter Defibrillator (WCD) with Power-Saving Function" which is incorporated herein by reference in its entirety. For example, the QRS detector module 216 may utilize a single channel out of the six possible differential channels.

The QRS detector module 216 utilizes a dual detection threshold for detecting different cardiac rhythm disorders. The dual detection threshold includes a first threshold and a second threshold. In some embodiments, the first QRS detector utilizes the first threshold 304 and the bradyarrhythmia QRS detector, i.e., the second QRS detector, utilizes the second threshold (not shown). The first and second thresholds are suitably positioned and utilized for detecting the different cardiac rhythm disorders. During the tachyarrhythmia disorder or condition, the ECG signal 302 tends to have an amplitude lesser than amplitude of an ECG signal of the patient 102 without tachyarrhythmia. Hence, for detecting the tachyarrhythmia condition, the first threshold 304 should be more sensitive than the second threshold. On the other hand, to avoid oversensing of the ECG signal 302 during the bradyarrhythmia condition and to avoid inhibiting therapy for the bradyarrhythmia condition, the second threshold should be less sensitive and more specific as compared with the first threshold 304.

Parameters of the first threshold 304 and the second threshold are adjusted or configured to avoid P-wave and T-wave oversensing. For the purpose of simplicity and clarity, operations related to only the first QRS detector and the first threshold 304 are described. However, operations related to the second QRS detector and the second threshold are implemented in a similar manner but with one or more different parameters to achieve the difference in sensitivity.

The first threshold 304, which is set at the initial position 308, begins to decay to form a decaying portion 310 where the value of the first threshold 304 reduces with time. The first QRS detector, also referred to as the first detector, compares magnitudes or value of the ECG signal 302 to corresponding values of the first threshold 304, continuously. After determining that level or the value of the ECG signal 302 is greater than the first threshold 304, a QRS complex 306 is deemed detected. In an example, the first detector identifies or detects an event, also referred to as a sensed event, when the magnitude of the ECG signal 302 or when an absolute value of a peak of the QRS complex 306 of the ECG signal 302 exceeds the value of the first threshold 304, at a detection position 312.

Upon the identification of the sensed event at the detection position 312, the first detector begins to observe a refractory period (labeled as "refrac" in FIG. 3). The first detector configures the duration of the refractory period for covering a duration of the detected QRS complex 306. In some embodiments, the refractory period is set to 160 ms or may be set in the range from 120 ms to 240 ms for the tachyarrhythmia detection. In some embodiments, for the bradyarrhythmia/asystole rhythm detection, the refractory period is set to 200 ms or may be set in the range from 160 ms to 320 ms.

The detection or identification of the events is prevented or inhibited by the first detector until the end of the refractory period, indicated by a refractory period end position 314 in FIG. 3. The prevention of identification of events during the refractory period restricts consideration of rectified peaks subsequent to the initially detected peak of the detected QRS complex 306, as additional QRS complexes of the ECG signal 302. During the refractory period, the first detector measures a maximum absolute ECG signal amplitude (maxQRS) 316 of the detected QRS complex 306.

At the refractory period end position 314, the first detector recalculates the value of the first threshold 304 based on the maxQRS 316. The first detector then sets the first threshold 304 to a value that is starting threshold value (THstart) 318, corresponding to the maxQRS 316 of the recently detected QRS complex 306. The THstart 318 is calculated using equation 1:

$$THstart=StartDrop*maxQRS \quad \text{Equation 1}$$

In some embodiments, the StartDrop of equation 1 is a coefficient that can be preset. For example, the StartDrop may be set to 0.75 for the tachyarrhythmia detection i.e., 75% of maxQRS 316. In some embodiments, the StartDrop may be set in the range from 0.5 to 1.0 for the tachyarrhythmia detection. A larger drop in the value of the THstart 318, in comparison with the maxQRS 316, results in an increased sensitivity of the first threshold 304. In some embodiments, the THstart 318 is lower than the maxQRS 316 to avoid under-sensing after a large spike or peak in the ECG signal 302. In some embodiments, for the bradyarrhythmia/asystole rhythm detection, the StartDrop may be set to 0.75 or may be set in the range from 0.75 to 1.0, depending on the desired sensitivity or specificity.

After setting the value of the first threshold 304 to the THstart 318, the first threshold 304 begins to decay with time in an exponential manner to form a decaying portion 320. The exponential decay of the first threshold 304 or rate of decaying of the first threshold 304 is represented by the decaying portion 320. The rate of decaying, referred to as TH(t), is calculated using equation 2:

$$TH(t) = THstart \cdot e^{-\frac{t}{\tau}} \quad \text{Equation 2}$$

In some embodiments, the time constant τ of equation 2 is preset. In some embodiments, τ may be set at 0.35 seconds or τ may be set in the range from 0.2 seconds to 0.5 seconds for tachyarrhythmia detection. In some embodiments, for the bradyarrhythmia/asystole rhythm detection, τ may be set at 0.5 seconds or τ may be set in the range from 0.35 seconds to 1 second, depending on the desired sensitivity or specificity.

The first threshold 304 stops decaying or decreasing upon reaching a minimum value 322, also referred to as minTh 322. The minTh 322 is based on the recently determined maxQRS 316, a ramp limit, a predetermined minimum floor value (MinFloor), and sense margin ratio (SMR). The minTh 322 is calculated using equation 3:

$$minTh=min(max(maxQRS/SMR, MinFloor), ramp\ limit/SMR) \quad \text{Equation 3}$$

The SMR is a scaling factor used for defining how much the first threshold 304 is allowed to decay. In some embodiments, the SMR may be set to 4 or set in the range from 2 to 6 for the tachyarrhythmia detection. In some embodiments, for the bradyarrhythmia/asystole rhythm detection, the SMR may be set to 2 or may be set in the range from 2 to 4, depending on the desired sensitivity or specificity.

The MinFloor is a preset value or a constant that is a lowest value reachable by the first threshold 304. In some embodiments, the MinFloor may be set to 25 μV with a range of 20 μV to 50 μV for the tachyarrhythmia detection, and the MinFloor may be set to 40 μV with a range of 30 μV to 60 μV for the bradyarrhythmia/asystole rhythm detection. The first detector utilizes the ramp limit value to limit peak value of the ECG signal 302 to be detected or sensed by the first threshold 304 in noisy conditions. In some embodiments, the ramp limit value may be preset. For example, the ramp limit value may be set to 1.6 mV or may be set in the range from 0.5 mV to 3 mV for the tachyarrhythmia detection. In some embodiments, for the bradyarrhythmia/asystole rhythm detection, the ramp limit value may be set to 3 mV or may be set in the range from 0.5 mV to 5 mV, depending on the desired sensitivity or specificity. In some embodiments, the ramp limit/SMR fraction of equation 3 may be a default or an initial value of the first threshold 304 when the WMS 100 powers up and/or is reset. In some embodiments, value of the minTh 322 is a value that is larger among one third of the maxQRS 316 or 25 μV.

For example, if the SMR is 3 and the maxQRS 316 is 1.2 mV, then ratio of maxQRS/SMR of the equation 3 is 400 μV. The value of the MinFloor is set to 25 μV. Further, the ramp limit is set to 1.6 mV, then the ratio ramp limit/SMR is 533 μV. For determining the minTh 322, the first detector determines a value larger among maxQRS/SMR and MinFloor and then a value lower among the determined value and the ramp limit/SMR ratio. Based on the determination, the first detector considers the determined lower value as the minTh 322.

The first detector maintains the minTh 322 for a predetermined time period. When the first detector does not detect or identify a new event until completion of the predetermined time period, the first threshold 304 decays with time from minTh 322 towards the MinFloor, which is the minimum threshold floor. However, if the first detector detects a new event within the predetermined time period, the first detector observes the refractory period. The first detector detects the subsequent ECG signal using the plurality of ECG electrodes 106-112 after the refractory period. The first detector, upon detecting the subsequent ECG signal or another QRS complex 328 of the ECG signal 302 at a detection point 324, determines if the subsequent ECG signal or the QRS complex 328 exceeds the first threshold 304. On determining that the subsequent ECG signal or the QRS complex 328 exceeds the first threshold 304, maxQRS 330 of the currently detected QRS complex 328 of the ECG signal 302 or of the subsequent ECG signal is determined during the refractory period. The first detector then recalculates the value of the first threshold 304, that is the THstart 318, using equation 1 based on the maxQRS 330 of the currently detected QRS complex 328 of the ECG signal 302 or of the subsequent ECG signal. The first threshold 304 is then set to the THstart 318 after the refractory period. The first detector iteratively calculates and sets values of the first threshold 304 based on at least the detection of QRS complexes, maximum absolute ECG signal amplitude, and the like, in the ECG signal 302 or the subsequent ECG signal. Therefore, each time a QRS complex is detected, the first threshold 304 is recalculated so that it may be used in detecting a subsequent QRS complex.

The first detector stores information regarding at least instances or time information related to the detected QRS complexes. Based on the stored information, one or more modules of the external defibrillator 200 determine the heart rate of the patient 102 and subsequently determine a presence or absence of the cardiac rhythm disorder such as tachyarrhythmia. On the other hand, the second QRS detector, also referred to as the second detector, stores information regarding at least instances or time information related to the detected QRS complexes. Based on the stored information, the one or more modules of the external defibrillator 200 determine the heart rate of the patient 102 and subsequently determine the presence or absence of the cardiac rhythm disorder such as bradyarrhythmia and/or asystole. For example, if the heart rate goes above 170 beats per minute (bpm), the one or more modules of the external defibrillator 200 determine that the patient 102 is currently suffering from the tachyarrhythmia condition based on the information from the first detector.

In the case of the bradyarrhythmia condition, for example, if an event is not detected within a predetermined interval, such as a pacing interval, subsequent to a first detected event, then the second QRS detector determines the presence of bradyarrhythmia. In some embodiments, the advice module 218 determines the heart rate of the patient 102 and subsequently determines the presence or absence of the cardiac rhythm disorder. Upon determining the presence of the tachyarrhythmia condition, the WMS 100 delivers the defibrillation shock to the patient 102 or upon determining the presence of bradyarrhythmia condition or asystole condition, the WMS 100 delivers the pacing pulse to the patient 102, as the therapy.

In some embodiments, for a QRS detector, the first threshold and the second threshold function independently without interaction with each other. Since the first QRS detector and the second QRS detector utilize the first threshold and the second threshold, respectively, for detection of different cardiac rhythm disorders, only one of the first threshold and the second threshold may detect a new sensed event. For example, only the first threshold may detect the new sensed event while the second threshold may not detect any event. Further, after one of the first threshold and the second threshold detects the new sensed event, the corresponding QRS detector may observe the refractory period whereas the other QRS detector may not observe the refractory period. As an example, if the first threshold detects the new sensed event, then the first QRS detector observes the refractory period whereas the second QRS detector does not observe the refractory period.

In some embodiments, the detection module 214, which includes the first detector and the second detector, uses a single threshold, such as the first threshold 304. The first detector and the second detector simultaneously and continuously measure peak of the ECG signals and vary values of the first threshold 304 accordingly, as described above, for identifying either the tachyarrhythmia or the bradyarrhythmia conditions, respectively.

In some embodiments, the QRS detector module 216 utilizes a single ECG vector based on the vector selection algorithm. If, however, multiple vectors are used, then a designated QRS detector module is assigned to each vector. In alternate embodiments, if multiple QRS detector modules are running simultaneously, a heart rate decision logic can be applied, for example, the lowest HR or the second lowest HR.

In some embodiments, the threshold parameters such as the start drop coefficient, the time constant τ, the scaling factor SMR, the preset value such as the MinFloor, and the peak value such as the ramp limit, of equations 1, 2, and 3, are empirically derived. In some embodiments, the QRS detector module 216 receives filtered ECG signals, based on which, the QRS detector module 216 modifies the empirically derived threshold parameters. The modification allows the first threshold 304 and second threshold to be set or positioned in a way such that the first detector and the second detector accurately determine the tachyarrhythmia and the bradyarrhythmia conditions, respectively, based on the filtered ECG signals. In some embodiments, the WMS 100 includes a filter for filtering the ECG signals from the ECG electrodes 106-112. In some embodiments, the ECG signals from the ECG electrodes 106-112 are filtered by a filtering component external to the WMS 100.

Figure 4:
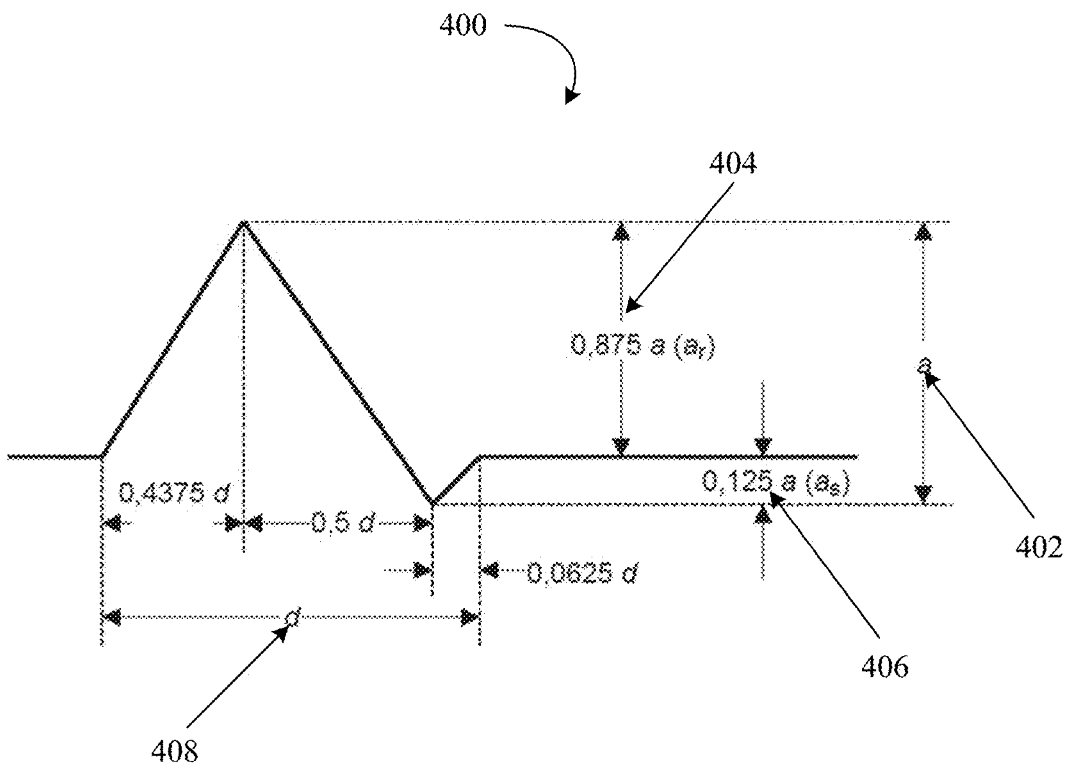
FIG. 4 illustrates a simulated standard QRS waveform obtained from a signal generator.

FIG. 4 illustrates a simulated standard QRS waveform 400 obtained from a signal generator. The simulated standard QRS waveform 400 is obtained from International Electrotechnical Commission (IEC), specifically from the IEC 60601-2-27:2011 standard. The simulated standard QRS waveform 400 supports in empirically deriving values for the threshold parameters to adjust the first threshold 304 and the second threshold for detecting and determining the tachyarrhythmia and the bradyarrhythmia/asystole conditions. As an exemplary embodiment, the simulated standard QRS waveform 400 depicted is a QRS complex which has an amplitude (a) 402 set at 1 mV peak to peak and a QRS duration (d) 408 set at 100 ms. The amplitude (a) 402 includes an amplitude of QR segment ($a_r$) 404 which is equal to 0.875 mV and amplitude of RS undershoot ($a_s$) 406 that is equal to 0.125 mV.

Figure 5:
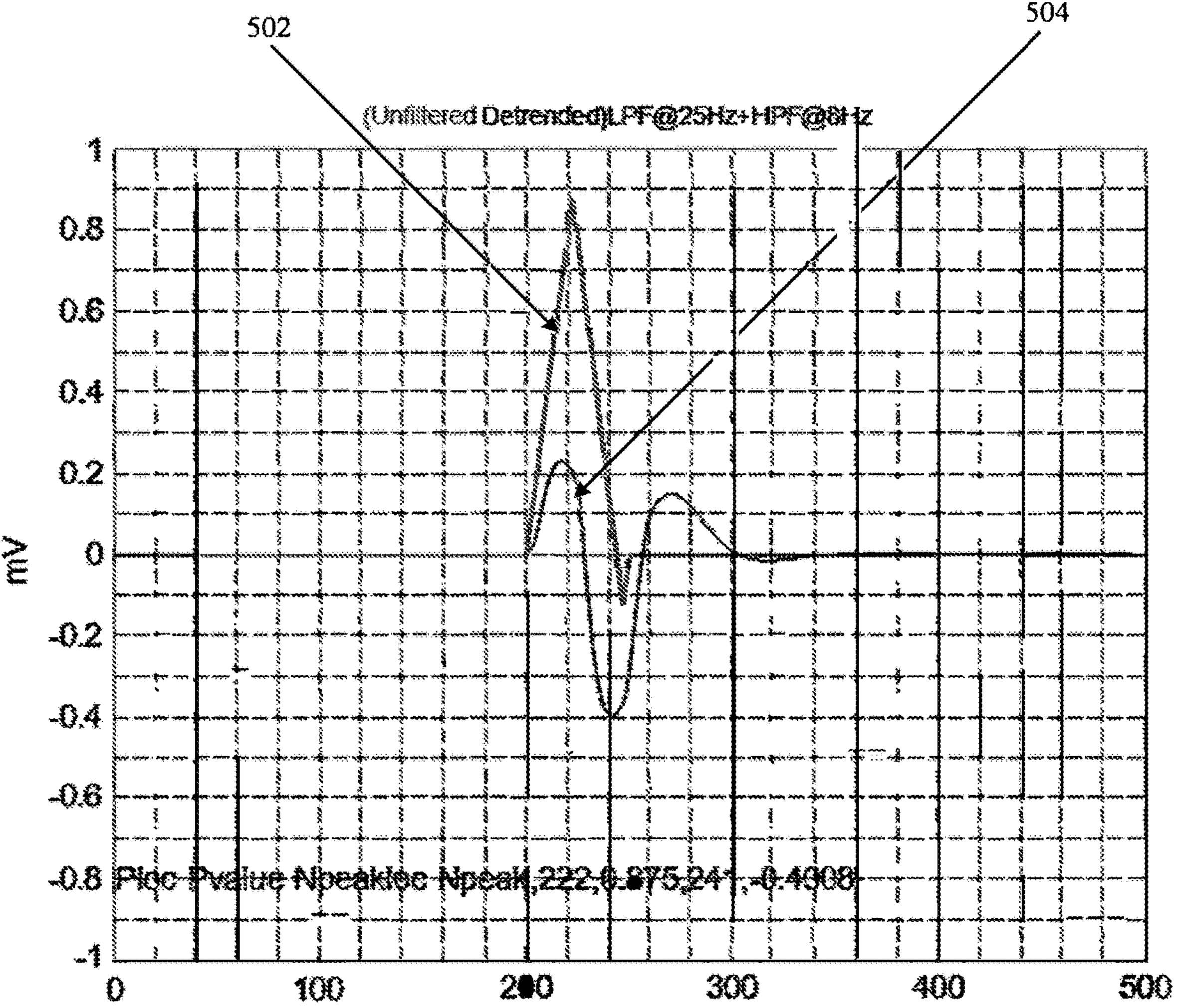
FIG. 5 illustrates an unfiltered ECG signal and a filtered ECG signal.

FIG. 5 illustrates an unfiltered ECG signal 502 and a filtered ECG signal 504. The unfiltered ECG signal 502 is similar to the simulated standard QRS waveform 400, as disclosed in FIG. 4. In some embodiments, the ECG signals from the ECG electrodes 106-112, as disclosed in FIG. 2, are unfiltered and are affected by noise, such as high-frequency noise. The noisy ECG signals from the ECG electrodes 106-112 may lead to erroneous detection and determination of the tachyarrhythmia and bradyarrhythmia/asystole conditions by the QRS detector module 216. Further, when the ECG electrodes 106-112 sense or obtain the ECG signals, the ECG signals have a Direct Current (DC) offset and an issue of baseline drifting. Therefore, the ECG signals have to be filtered by a high pass filter to overcome issues such as the DC offset and the baseline drifting. The ECG signals may also have to be filtered using a low pass filter to eliminate the high-frequency noise. For example, a notch filter may be utilized for the elimination of the high-frequency noise. In some embodiments, the WMS 100 includes the filter, such as the high pass filter, the low pass filter, and the like, for filtering the ECG signals from the ECG electrodes 106-112. In some embodiments, the filters, such as the high pass filter, the low pass filter, and the like, also referred to as the filtering component, may be external to the WMS 100.

In some embodiments, the unfiltered ECG signal 502 is filtered using both a high pass filter with a cutoff frequency at 8 Hz and a low pass filter with a cutoff frequency at 25 Hz. In some embodiments, the cut-off frequencies of the filters used may be geography specific. In some embodiments, different filters may be used to filter the ECG signals. The unfiltered ECG signal 502 is a 1 mV peak-to-peak waveform and the filtered ECG signal 504 is a waveform with 0.4008 mV negative peak from the baseline. The filtered ECG signal 504 is provided to the QRS detector module 216, as disclosed in FIG. 2, which avoids erroneous detection of the cardiac rhythm disorders due to the noise, the DC offset, or the baseline drift. For the purpose of clarity, only the asystole condition of the cardiac rhythm disorders and the corresponding second detector and second threshold are considered for the explanation. The same explanation or process, with similar modifications to the parameters of the first threshold 304 may be considered for the tachyarrhythmia condition.

In an example, the second QRS detector would need to detect a 100 μV peak-to-peak signal for detecting a QRS complex in the unfiltered ECG signal 502. However, the filtered ECG signal 504 would have a reduced peak of 40 μV peak which cannot be detected by the second threshold that is set and configured based on the 100 μV peak-to-peak signal. The second QRS detector with the second threshold, calculated based on the unfiltered ECG signal 502, would be unable to detect the filtered ECG signal 504. To enable the detection of the QRS complexes, for example, in the filtered ECG signal 504, the threshold parameters of the second threshold of the second detector are modified or adjusted accordingly based on the characteristics of the filtered ECG signal 504. The threshold parameters of the second threshold that are modified include SMR, MinFloor, and ramp limit for bradyarrhythmia/asystole detection based on the 40 μV peak amplitude of the filtered ECG signal 504. The first threshold 304 is adjusted to detect QRS complexes of the ECG signal 302 since the amplitudes of the QRS complexes are shrunken when the heart experiences tachyarrhythmia compared to a QRS complex during a normal heart condition. With the modified parameters, the QRS complexes of the filtered ECG signal 504 with peak-to-peak values less than 40 μV would not be deemed "detected" and may be considered as asystole.

Since embodiments of the QRS detector module 216 as disclosed in FIG. 2 use a rectified peak amplitude, baseline to peak amplitude is adjusted based on characteristics of the filter used i.e., the peak amplitude of 0.4008 mV or 40 μV after filtering will correspond to an unfiltered peak amplitude of 1 mv or 100 μV.

In another example, the second QRS detector would detect a 150 μV peak-to-peak voltage of an unfiltered ECG signal, and signals with peak-to-peak voltage below 150 μV would be deemed not to be a QRS complex of the unfiltered ECG signal. After filtering the unfiltered ECG signal, the 150 μV peak-to-peak voltage of the unfiltered ECG signal would have a filtered ECG signal with a peak-to-peak voltage of 60 μV. To enable the detection of the QRS complexes, the threshold parameters of the second threshold of the second detector are modified accordingly based on the characteristics of the filtered ECG signal. Thus, the second detector does not deem the QRS complexes of the filtered ECG signal with peak-to-peak voltage less than 60 μV as "detected" and may consider the condition as asystole.

Similar to modifying the second threshold based on the characteristics of the filtered ECG signal for detecting the bradyarrhythmia/asystole rhythm disorder, the first threshold is modified based on the characteristics of the filtered ECG signal for detecting the tachyarrhythmia.

In some embodiments, the second detector only detects a QRS complex if the first detector detects a peak in the refractory period that is greater than minimum threshold minTh for bradyarrhythmia/asystole rhythm detection. For example, if the minimum threshold for bradyarrhythmia/asystole rhythm detection is set to 40 μv and the first detector detects a peak in the refractory period greater than 40 μV, then, such a QRS complex is counted as a brady/asystole QRS event, and the associated heart rate is calculated.

Figure 6:
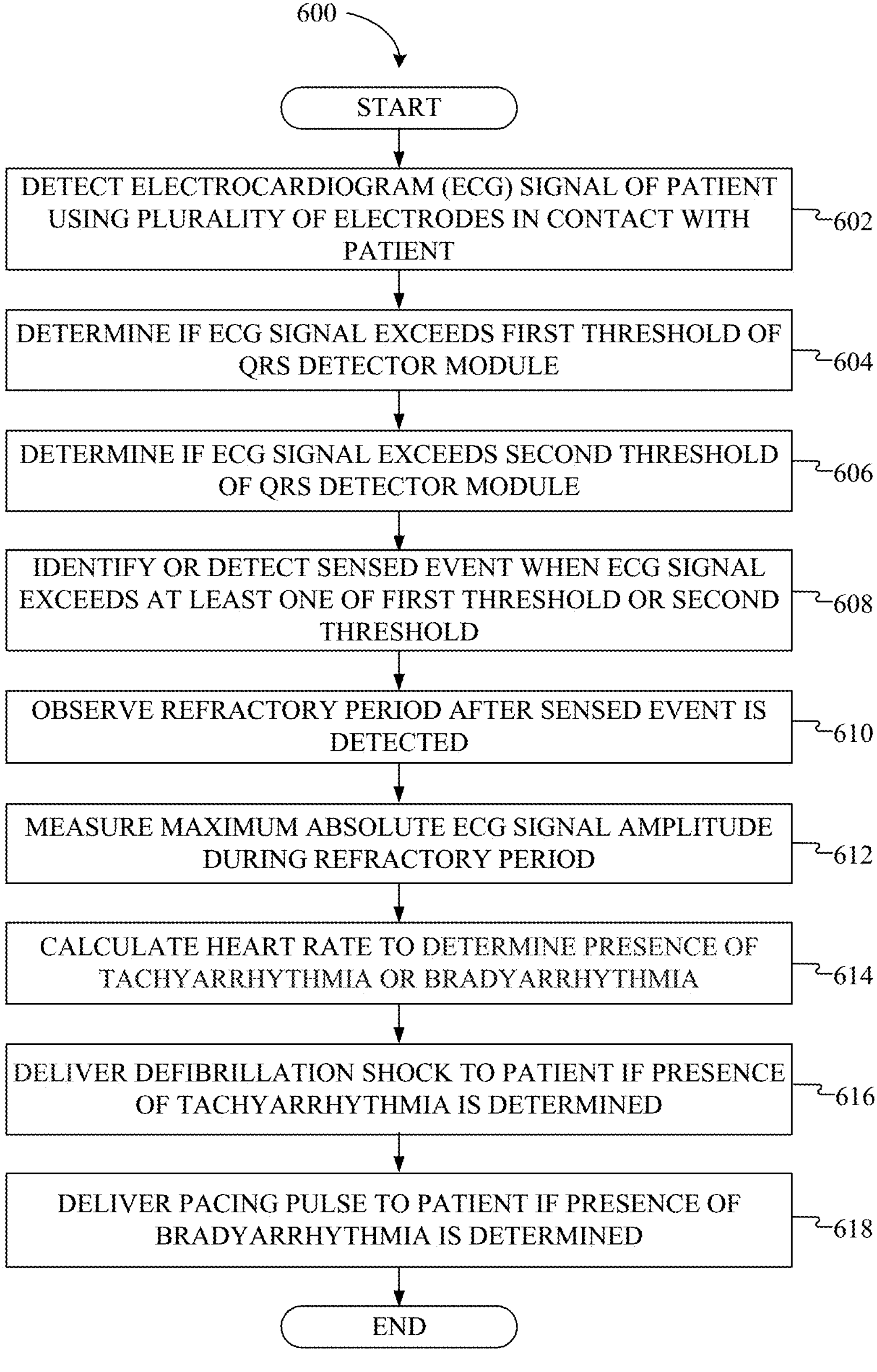
FIG. 6 illustrates an example method for identifying a cardiac condition using the WMS.

FIG. 6 illustrates an example method 600 for identifying a cardiac condition using the WMS 100, as disclosed in FIG. 1. The WMS 100 includes the QRS detector module 216, as disclosed in FIG. 2, for detecting the cardiac condition. The QRS detector module 216 includes the first detector and the second detector, as discussed in FIG. 2, which analyzes the ECG signals using the first threshold 304, as disclosed in FIG. 3, and the second threshold, respectively. The first threshold 304 is configured to identify the tachyarrhythmia condition and the second threshold is configured to identify the bradyarrhythmia/asystole condition.

Although the example method 600 depicts a particular sequence of operations, the sequence may be altered without departing from the scope of the present disclosure. For example, some of the operations depicted may be performed in parallel or in a different sequence that does not materially affect the function of the method 600. In other examples, different components of an example device or system that implements the method 600 may perform functions at substantially the same time or in a specific sequence.

According to some embodiments, the method 600 includes detecting an ECG signal of a patient using a plurality of electrodes, in contact with the patient, at block 602. For example, the WMS 100, as disclosed in FIG. 1, detects the ECG signal 302, as disclosed in FIG. 3, of the patient 102, using the plurality of electrodes such as the ECG electrodes 106-112, as disclosed in FIG. 2.

The method 600 further includes determining if the detected ECG signal exceeds a first threshold of a QRS detector module and determining if the detected ECG signal exceeds a second threshold of the QRS detector module, at blocks 604 and 606 respectively. For example, the first detector of the QRS detector module 216 determines if the ECG signal 302, as disclosed in FIG. 3, exceeds the first threshold 304 and the second detector of the QRS detector module 216 determines if the ECG signal 302 exceeds the second threshold.

The method 600 further includes identifying or detecting a sensed event when the detected ECG signal exceeds one of the first threshold and the second threshold, at block 608. For example, the QRS detector module 216 identifies/detects the event at the detection position 312, disclosed in FIG. 3, when the ECG signal 302 exceeds the first threshold 304 or identifies/detects an event when the ECG signal 302 exceeds the second threshold.

Further, the method 600 includes observing a refractory period after the sensed event is detected and measuring a maximum absolute ECG signal amplitude during the refractory period, at blocks 610 and 612, respectively. In an example, the QRS detector module 216 observes the refractory period after the sensed event is detected and measures the maximum absolute ECG signal amplitude (maxQRS) 316, as disclosed in FIG. 3, during the refractory period. The QRS detector module 216 is activated to inhibit identification or detection of a new sensed event during the refractory period.

Further, the QRS detector module 216 is activated to recalculate the first threshold 304 based on the maxQRS 316 during the refractory period and/or the QRS detector module 216 recalculates the second threshold based on the maxQRS 316 during the refractory period. The recalculation is performed by multiplying a start drop coefficient corresponding to the first detector and the second detector, by the maxQRS 316. Further, the QRS detector module 216 decreases at least one of the recalculated first threshold or the recalculated second threshold with time in an exponential manner. The QRS detector module 216 stops decreasing the recalculated first threshold 304 and recalculated second threshold when a minimum threshold level is reached.

Further, the QRS detector module 216 is activated to detect the subsequent ECG signal or another QRS complex 328, as disclosed in FIG. 3, in the ECG signal 302 using the ECG electrodes 106-112 in contact with the patient 102. Further, the QRS detector module 216 is reactivated to determine if the subsequent ECG signal or the recently detected QRS complex 328 exceeds the recalculated first threshold 304 or the recalculated second threshold.

The method 600 further includes calculating a heart rate to determine the presence of the tachyarrhythmia or the bradyarrhythmia condition at block 614. For example, the QRS complexes detected by the QRS detector module 216 may be used to determine the heart rate using the inverse of the R-R interval of the ECG signal 302 exceeding the first threshold. The method 600 includes delivering a defibrillation shock to the patient if the presence of tachyarrhythmia is determined and delivering a pacing pulse to the patient if the presence of bradyarrhythmia is determined, at blocks 616 and 618, respectively. For example, based on the detection of the tachyarrhythmia condition and advice from the advice module 218, the defibrillation shock is delivered to the patient 102 using the defibrillation electrodes 116, 118. Further, based on the detection of bradyarrhythmia and advice from the advice module 218, the pacing pulse is delivered to the patient 102 using the defibrillation electrodes 116, 118.

The WMS 100 delivers the defibrillation shock or the pacing pulse to the patient 102 if the recalculated first threshold 304 or the recalculated second threshold, respectively, is exceeded.

The WMS 100, along with the corresponding method 600, is utilized for a non-invasive process of simultaneously detecting cardiac rhythm disorders and providing therapy to the patient based on the detected cardiac rhythm disorders. The WMS 100 is a single sensing mechanism that is capable of detecting different cardiac rhythm disorders using thresholds whose specificity and sensitivity are configured. The thresholds, with the configured specificity and sensitivity, support accurate detection of different cardiac rhythm disorders. The WMS 100 is also capable of providing the therapy such as defibrillation shocks or pacing pulses based on the detected cardiac rhythm disorder. Therefore, the WMS 100, along with the corresponding method 600, is capable of detecting cardiac rhythm disorders, such as tachyarrhythmia, bradyarrhythmia, and asystole accurately, thereby reducing risk of an incorrect detection compared to the conventional QRS detectors.

Other embodiments include combinations and sub-combinations of features described or shown in the drawings herein, including for example, embodiments that are equivalent to: providing or applying a feature in a different order than in a described embodiment, extracting an individual feature from one embodiment, and inserting such feature into another embodiment; removing one or more features from an embodiment; or both removing one or more features from an embodiment and adding one or more features extracted from one or more other embodiments while providing the advantages of the features incorporated in such combinations and sub-combinations. As used in this paragraph, feature or features can refer to the structures and/or functions of an apparatus, article of manufacture or system, and/or the steps, acts, or modalities of a method.

These and other changes can be made to the embodiments in light of the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

What is claimed is:

1. A wearable medical system, comprising:
- a support structure;
- a plurality of electrocardiogram (ECG) electrodes to sense an ECG signal of a patient;
- an energy output device to store an electrical charge;
- an output circuit coupled to the energy output device;
- a plurality of therapy electrodes, coupled to the support structure and the output circuit, wherein the plurality of therapy electrodes deliver therapy to the patient; and
- a processor, coupled to the plurality of ECG electrodes and the output circuit, comprising:
  - a QRS detector module, wherein the QRS detector module has a first threshold and a second threshold, and configured to:
    - detect a sensed event responsive to the ECG signal exceeding at least one of the first threshold or the second threshold;
    - observe a refractory period after the sensed event is detected;
    - inhibit identification or detection of a new sensed event during the refractory period;
    - measure a maximum absolute ECG signal amplitude during the refractory period;
    - recalculate the first threshold and/or the second threshold based on the maximum absolute ECG signal amplitude during the refractory period;
    - detect a subsequent ECG signal after the refractory period using the plurality of ECG electrodes in contact with the patient; and
    - determine whether the subsequent ECG signal exceeds the recalculated first threshold or the recalculated second threshold.

2. The wearable medical system of claim 1, wherein the QRS detector module further comprises:
- a first QRS detector, wherein the first QRS detector analyzes ECG signals for the first threshold; and
- a second QRS detector, wherein the second QRS detector analyzes ECG signals for the second threshold.

3. The wearable medical system of claim 1, further comprising a user interface, wherein the user interface comprises audio and/or visual alarms.

4. The wearable medical system of claim 1, wherein the first threshold is configured to detect tachyarrhythmia and the second threshold is configured to detect bradyarrhythmia.

5. The wearable medical system of claim 1, wherein when the recalculated first or second threshold is exceeded, a heart rate is calculated; wherein the heart rate is used to determine the presence of tachyarrhythmia or bradyarrhythmia; and wherein a defibrillation shock is delivered to the patient by the plurality of therapy electrodes when the presence of tachyarrhythmia is determined, or a pacing pulse is delivered to the patient by the plurality of therapy electrodes when the presence of bradyarrhythmia is determined.

6. The wearable medical system of claim 1, further comprising a band pass filter for filtering ECG signals.

7. A method for identifying a cardiac condition using a wearable medical system having a processor and a memory, the method comprising:
- detecting an electrocardiogram (ECG) signal of a patient using a plurality of electrodes in contact with the patient;
  - determining whether the ECG signal exceeds a first threshold of a QRS detector module;
  - determining whether the ECG signal exceeds a second threshold of the QRS detector module;
  - identifying or detecting a sensed event responsive to the ECG signal exceeding at least one of the first threshold or the second threshold;
  - observing a refractory period after the sensed event is detected;
  - inhibiting identification or detection of a new sensed event during the refractory period;
  - measuring a maximum absolute ECG signal amplitude during the refractory period;
  - recalculating the first threshold and/or the second threshold based on the maximum absolute ECG signal amplitude during the refractory period;
  - detecting a subsequent ECG signal after the refractory period using the plurality of electrodes in contact with the patient;

determining whether the subsequent ECG signal exceeds the recalculated first threshold or the recalculated second threshold;

calculating, based on determination that the subsequent ECG signal exceeds the recalculated first threshold or the recalculated second threshold of the QRS detector module, a heart rate to determine the presence of tachyarrhythmia or bradyarrhythmia;

delivering a defibrillation shock to the patient when the presence of tachyarrhythmia is determined; and delivering a pacing pulse to the patient when the presence of bradyarrhythmia is determined.

8. The method of claim 7, wherein the first threshold and/or the second threshold are recalculated by multiplying a start drop coefficient by the maximum absolute ECG signal amplitude.

9. The method of claim 7, further comprising decreasing at least one of the recalculated first threshold or the recalculated second threshold with time in an exponential manner.

10. The method of claim 7, wherein the recalculated first threshold and the recalculated second threshold stop decreasing when the recalculated first threshold and the recalculated second threshold reach a minimum threshold level.

11. The method of claim 7, wherein the heart rate is calculated using an inverse of an R-R interval of the ECG signals exceeding the first threshold and the recalculated first threshold or exceeding the second threshold and the recalculated second threshold.

12. The method of claim 7, wherein the first threshold is configured to identify tachyarrhythmia and the second threshold is configured to identify bradyarrhythmia.

13. The method of claim 7, wherein the QRS detector module comprises:

a first QRS detector, wherein the first QRS detector analyzes ECG signals for the first threshold; and a second QRS detector, wherein the second QRS detector analyzes ECG signals for the second threshold.

14. A non-transitory computer-readable medium encoded with QRS detection instructions stored thereon that, when executed by a computing device, cause the computing device to perform operations for identifying a cardiac condition in a patient, the operations comprising:

detecting an electrocardiogram (ECG) signal using one or more ECG electrodes;

activating a QRS detector module to:

analyze the ECG signal, wherein the QRS detector module has a first threshold and a second threshold;

determine whether the ECG signal exceeds the first threshold or the second threshold;

identify or detect a sensed event responsive to the ECG signal exceeding the first threshold or the second threshold;

observe a refractory period after the sensed event is detected;

inhibit identification or detection of a new sensed event during the refractory period;

measure a maximum absolute ECG signal amplitude during the refractory period;

recalculate the first threshold and/or the second threshold based on the maximum absolute ECG signal amplitude during the refractory period;

detecting a subsequent ECG signal after the refractory period using the one or more ECG electrodes;

reactivating the QRS detector module to determine whether the subsequent ECG signal exceeds the recalculated first threshold or the recalculated second threshold;

calculate, based on a determination that the subsequent ECG signal exceeds the recalculated first threshold or the recalculated second threshold, a heart rate to determine the presence of tachyarrhythmia or bradyarrhythmia; and controlling an output circuit and an energy output device to:

deliver a defibrillation shock to the patient through a plurality of therapy electrodes when the presence of tachyarrhythmia is determined; and deliver a pacing pulse to the patient through a plurality of therapy electrodes when the presence of bradyarrhythmia is determined.

15. The non-transitory computer-readable medium of claim 14, wherein the first threshold and/or the second threshold are recalculated by multiplying a start drop coefficient by the maximum absolute ECG signal amplitude.

16. The non-transitory computer-readable medium of claim 14, wherein the operations further include decreasing at least one of the recalculated first threshold or the recalculated second threshold with time in an exponential manner until the recalculated first threshold and/or the recalculated second threshold reach a minimum threshold level.

17. The non-transitory computer-readable medium of claim 14, wherein the heart rate is calculated using an inverse of an R-R interval of the ECG signals exceeding the first threshold and the recalculated first threshold or exceeding the second threshold and the recalculated second threshold.

18. The non-transitory computer-readable medium of claim 14, wherein the first threshold is configured to further detect tachyarrhythmia and the second threshold is configured to further detect bradyarrhythmia.

* * * * *